(12) United States Patent
Kishida et al.

(10) Patent No.: US 9,580,446 B2
(45) Date of Patent: Feb. 28, 2017

(54) GAS SEPARATION MATERIAL USING METAL COMPLEX AND GAS SEPARATION METHOD

(71) Applicant: SHOWA DENKO K.K., Tokyo (JP)

(72) Inventors: Keisuke Kishida, Oita (JP); Yoshihiro Watanabe, Oita (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 14/443,573

(22) PCT Filed: Dec. 16, 2013

(86) PCT No.: PCT/JP2013/083629
§ 371 (c)(1),
(2) Date: May 18, 2015

(87) PCT Pub. No.: WO2014/103778
PCT Pub. Date: Jul. 3, 2014

(65) Prior Publication Data
US 2015/0329563 A1 Nov. 19, 2015

(30) Foreign Application Priority Data
Dec. 26, 2012 (JP) .................. 2012-283247

(51) Int. Cl.
*C07F 1/08* (2006.01)
*B01D 53/04* (2006.01)
(Continued)

(52) U.S. Cl.
CPC ............... *C07F 1/08* (2013.01); *B01D 53/02* (2013.01); *B01D 53/047* (2013.01);
(Continued)

(58) Field of Classification Search
CPC .. B01D 53/02; B01D 53/0462; B01D 53/047; B01D 53/228; B01D 53/229;
(Continued)

(56) References Cited

U.S. PATENT DOCUMENTS 3,992,471 A 11/1976 Priegnitz
6,436,173 B1 * 8/2002 Jale .................. B01D 53/02
                                          162/164.2
(Continued)

FOREIGN PATENT DOCUMENTS

JP     51-43702 A     4/1976
JP     08-243385 A   9/1996
(Continued)

OTHER PUBLICATIONS

Mitsuru Kondo et al., Rational Synthesis of Stable Channel-Like Cavities with Methane Gas Adsorption Properties: [{Cu$_2$(pzdc)$_2$(L)}$_n$] (pzdc=pyrazine-2,3-dicarboxylate; L=a Pillar Ligand); Angew. Chem. Int. Ed., 1999, pp. 140-143, vol. 38, No. 1/2.
(Continued)

*Primary Examiner* — Jason M Greene
(74) *Attorney, Agent, or Firm* — Sughrue Mion, PLLC

(57) ABSTRACT

A separation material and method for separating and recovering a target gas from a mixed gas including the target gas and a hydrocarbon gas that has the same number of carbon atoms as the target gas, the target gas being a hydrocarbon gas having 2 or 4 carbon atoms and a carbon-carbon double bond. This gas separation material includes: a metal complex containing a 2,3-pyrazinedicarboxylic acid; an ion of at least one type of metal (M); and an organic ligand (B) capable of bidentate coordination to the metal ion represented by general formula (1) or general formula (2), where (M), formula (1) and formula (2) are as defined herein. The
(Continued)

metal complex has a composition represented by $M^{2+}_2 A^{2-}_2 B$ where $M^{2+}$ is the ion of the metal (M), $A^{2-}$ is a 2,3-pyrazinedicarboxylate dianion and B is the organic ligand (B) capable of bidentate coordination to the metal ion.

13 Claims, 9 Drawing Sheets

(51) Int. Cl.
| | |
|---|---|
| *B01D 53/047* | (2006.01) |
| *B01D 53/22* | (2006.01) |
| *B01J 20/28* | (2006.01) |
| *C07C 7/144* | (2006.01) |
| *B01J 20/22* | (2006.01) |
| *B01J 20/24* | (2006.01) |
| *B01J 20/26* | (2006.01) |
| *C07C 7/12* | (2006.01) |
| *B01D 53/02* | (2006.01) |
| *D21H 17/12* | (2006.01) |
| *B01J 20/32* | (2006.01) |
| *B01D 71/02* | (2006.01) |
| *B01D 71/62* | (2006.01) |

(52) U.S. Cl.
CPC ....... *B01D 53/0462* (2013.01); *B01D 53/228* (2013.01); *B01D 53/229* (2013.01); *B01D 71/022* (2013.01); *B01D 71/62* (2013.01); *B01J 20/223* (2013.01); *B01J 20/24* (2013.01); *B01J 20/261* (2013.01); *B01J 20/28033* (2013.01); *B01J 20/28038* (2013.01); *B01J 20/3212* (2013.01); *B01J 20/3265* (2013.01); *C07C 7/12* (2013.01); *C07C 7/144* (2013.01); *D21H 17/12* (2013.01); *B01D 53/22* (2013.01); *B01D 2252/2053* (2013.01); *B01D 2253/204* (2013.01); *B01D 2256/24* (2013.01); *B01D 2257/7022* (2013.01)

(58) Field of Classification Search
CPC ...... B01D 69/10; B01D 71/022; B01D 71/62; B01D 2253/204; B01D 2256/241; B01D 2256/245; B01D 2257/702; B01D 2257/7022; B01J 20/223; B01J 20/226; B01J 20/24; B01J 20/261; B01J 20/3265; C07C 7/12; C07C 7/13; C07C 7/144; C07F 1/08; C07F 3/02; C07F 3/04; C07F 3/06; C07F 15/00; C07F 15/04; C07F 15/06

See application file for complete search history.

(56) References Cited

U.S. PATENT DOCUMENTS

| | | | | |
|---|---|---|---|---|
| 7,637,983 | B1* | 12/2009 | Liu | ............... B01J 20/226 210/500.21 |
| 2007/0219280 | A1 | 9/2007 | Kitagawa et al. | |
| 2008/0214806 | A1* | 9/2008 | Schubert | ............... B01D 53/02 544/226 |
| 2015/0144085 | A1* | 5/2015 | Inubushi | ............... B01D 53/02 123/1 A |
| 2015/0165415 | A1* | 6/2015 | Inubushi | ............... B01D 53/047 546/2 |

FOREIGN PATENT DOCUMENTS

| | | |
|---|---|---|
| JP | 09-227572 A | 9/1997 |
| JP | 2004-196594 A | 7/2004 |
| JP | 2005-255651 A | 9/2005 |
| JP | 3746321 B2 | 2/2006 |
| JP | 2007-063269 A | 3/2007 |
| JP | 2008-184509 A | 8/2008 |
| JP | 2008-184533 A | 8/2008 |
| JP | 4217776 B2 | 2/2009 |
| JP | 2010-121079 A | 6/2010 |
| WO | 2011/105521 A1 | 9/2011 |

OTHER PUBLICATIONS

Ryotaro Matsuda et al., "Highly controlled acetylene accommodation in a metal-organic microporous material", Nature, Jul. 14, 2005, pp. 238-241, vol. 436.

Ryo Kitaura et al, "Formation and Characterization of Crystalline Molecular Arrays of Gas Molecules in a 1-Dimensional Ultramicropore of a Porous Copper Coordination Polymer", Journal of Physical Chemistry B, 2005, pp. 23378-23385, vol. 109, No. 49.

International Search Report of PCT/JP2013/083629 dated Mar. 18, 2014 [PCT/ISA/210].

* cited by examiner

GAS SEPARATION MATERIAL USING METAL COMPLEX AND GAS SEPARATION METHOD

CROSS REFERENCE TO RELATED APPLICATIONS

This application is a National Stage of International Application No. PCT/JP2013/083629, filed Dec. 16, 2013, claiming priority based on Japanese Patent Application No. 2012-283247, filed Dec. 26, 2012,the contents of all of which are incorporated herein by reference in their entirety.

TECHNICAL FIELD

The present invention relates to a gas separating material containing a specific metal complex and a method for separating a hydrocarbon gas from a mixed gas using the gas separating material.

BACKGROUND ART

Separating and recovering the target hydrocarbon gas (e.g., ethylene and 1,3-butadiene) from a mixed gas containing hydrocarbons are known technology.

An example of a hydrocarbon gas to be separated and recovered is ethylene. Ethylene is an important chemical compound as a raw material for various products in synthetic chemical industries, such as ethylene oxide, vinyl chloride, acetaldehyde, styrene, and polyethylene.

Ethylene is generally produced by naphtha cracking or dehydrogenation of ethane. Ethylene is recovered as a distillate fraction having 2 carbon atoms, which contains the target ethylene as well as other compounds, such as ethane. Therefore, it is necessary to selectively separate and recover ethylene from the mixture produced. One method for separating is distillation. However, since the boiling point of ethylene is close to that of ethane, cryogenic separation under high pressure at low temperature is necessary, and as a result, consumes a lot of energy.

A method for separating and recovering ethylene more energy-effectively includes separation by adsorption. When a mixed gas is separated by pressure swing adsorption or temperature swing adsorption, in general, a molecular sieving carbon, zeolite, and the like is used as an adsorption material, and separation is achieved by the differences in its equilibrium adsorption amount or adsorption rate. However, when a mixed gas is separated by utilizing the differences in equilibrium adsorption amount of each component gas, since the conventional adsorption materials cannot selectively adsorb only the gas to be removed, the separation factor becomes smaller, which results in an increase in the size of an apparatus.

Another example of a hydrocarbon gas to be separated and recovered is 1,3-butadiene. 1,3-butadiene is useful compound as, for example, a raw material for the production of a synthetic rubber, as well as an intermediate of enormous compounds. 1,3-Butadiene is generally produced by naphtha cracking or dehydrogenation of butene. In these production methods, 1,3-butadiene is obtained as one component of a mixed gas. Therefore, it is necessary to selectively separate and recover 1,3-butadiene from the products obtained as mixtures. The principal components having 4 carbon atoms in the products may be 1,3-butadiene, isobutene, 1-butene, 2-butene, normal butane, and isobutane. These have the same carbon number and close boiling points, and thus it is difficult to carry out separation by distillation that is usually used in industrial scale.

One of the other separation methods includes extractive distillation. Since this method is an absorption method using polar solvents, so much energy is used when 1,3-butadiene is recovered from the polar solvents. Therefore, separation by an adsorption method is desirable as a method for separating and recovering 1,3-butadiene with reduced energy.

However, since conventional porous materials (Patent Literature 1) have low separation performance, multistage separation is required, which results in an increase in the size of a separation apparatus.

As an adsorption material providing excellent separation performance, a porous metal complex, in which dynamic structural changes occur by an external stimulus, has been developed. When this porous material is used as a gas adsorption material, it has been observed that gas is not adsorbed below a certain pressure, but gas adsorption occurs above a certain pressure, which is a particular characteristic of the material. In addition, it has been observed that there is a characteristic in which a pressure at which adsorption occurs differs depending on the type of gas subjected to adsorption.

When this porous material is applied to, for example, an adsorption material in a pressure swing adsorption-type gas separation apparatus, highly efficient gas separation can be achieved. In addition, the swing width of pressure can be narrowed, which contributes also to energy saving. Furthermore, since it can contribute to the downsizing of a gas separation apparatus, cost competitiveness can be enhanced when a highly pure gas is marketed as a product, and even when a highly pure gas is used within one's own factories, costs necessary for the facility that requires a highly pure gas can be reduced, and as a result, the cost for the production of final products can be reduced.

Patent Literatures 2 to 8 and Non Patent Literatures 1 to 3 disclose a metal complex $[Cu_2(pydc)_2(pyz)]$ of a copper ion, 2,3-pyrazinedicarboxylate dianion, and pyrazine. Although these documents have reported the adsorption properties of acetylene and methane, they have not mentioned the adsorption and separation of ethylene and hydrocarbon gases having 4 carbon atoms.

CITATION LIST

Patent Literature

[Patent Literature 1]
 Japanese Unexamined Patent Publication (Kokai) No. 51-43702
[Patent Literature 2]
 Japanese Patent No. 3746321
[Patent Literature 3]
 Japanese Patent No. 4217776
[Patent Literature 4]
 Japanese Unexamined Patent Publication (Kokai) No. 2005-255651
[Patent Literature 5]
 Japanese Unexamined Patent Publication (Kokai) No. 2007-063269
[Patent Literature 6]
 Japanese Unexamined Patent Publication (Kokai) No. 2008-184509

[Patent Literature 7]
Japanese Unexamined Patent Publication (Kokai) No. 2008-184533

[Patent Literature 8]
Japanese Unexamined Patent Publication (Kokai) No. 2010-121079

Non Patent Literature

[Non Patent Literature 1]
Mitsuru Kondo, Takashi Okubo, Akiko Asami, Shin-ichiro Noro, Tomomichi Yoshitomi, Susumu Kitagawa, Tomohiko Ishii, Hiroyuki Matsuzaka, and Kenji Seki, Angewandte Chemie International Edition, Vol. 38, pp. 140-143 (1999)

[Non Patent Literature 2]
Ryotaro Matsuda, Ryo Kitaura, Susumu Kitagawa, Yoshiki Kubota, Rodion V. Belosludov, Tatsuo C. Kobayashi, Hirotoshi Sakamoto, Takashi Chiba, Masaki Takata, Yoshiyuki Kawazoe, and Yoshimi Mita, Nature, Vol. 436, pp. 238-241 (2005)

[Non Patent Literature 3]
Ryo Kitaura, Ryotaro Matsuda, Yoshiki Kubota, Susumu Kitagawa, Masaki Takata, Tatsuo C. Kobayashi, and Megumi Suzuki, Journal of Physical Chemistry B, Vol. 109, pp. 23378-23385 (2005)

SUMMARY OF THE INVENTION

Problems to be Solved by the Invention

An object of the present invention is to provide a separating material and a separation method that are superior to the conventional ones, capable of separating and recovering the target gas defined as a hydrocarbon gas having a carbon-carbon double bond and having 2 to 5 carbon atoms, particularly hydrocarbon gas having a carbon-carbon double bond and having 2 or 4 carbon atoms, for example, ethylene or 1,3-butadiene, from a mixed gas containing the target gas and a hydrocarbon gas having the same number of carbon atoms as the target gas.

Means for Solving the Problems

As a result of diligent investigation, the present inventors have found that the above mentioned object can be achieved by using a metal complex of a particular metal M ion, 2,3-pyrazinedicarboxylate dianion, and an organic ligand (B) capable of bidentate coordination to an ion of the metal M as an adsorption material, and developed the present invention. Namely, the present invention includes the following Embodiments [1] to [19].

[1] A gas separating material that selectively separates the target gas defined as a hydrocarbon gas having a carbon-carbon double bond and having 2 or 4 carbon atoms from a mixed gas containing the target gas and a hydrocarbon gas having the same number of carbon atoms as the target gas, comprising a metal complex of:
   2,3-pyrazinedicarboxylic acid;
   at least one metal M ion selected from the group consisting of beryllium, magnesium, calcium, strontium, barium, titanium, vanadium, chromium, manganese, iron, ruthenium, cobalt, rhodium, nickel, palladium, platinum, copper, zinc, and cadmium;

an organic ligand (B) capable of bidentate coordination to the metal ion, represented by the following general formula (1):

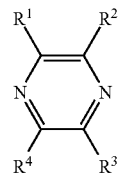

or the following general formula (2):

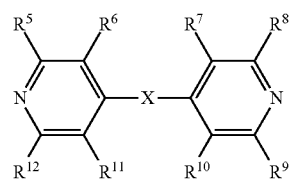

wherein X is any of —$CH_2$—, —$CH_2$—$CH_2$—, —$CH_2$—$CH_2$—$CH_2$—, —CH=CH—, —C≡C—, —O—, —S—, —S—S—, —N=N—, or —NHCO—, and $R^1$, $R^2$, $R^3$, $R^4$, $R^5$, $R^6$, $R^7$, $R^8$, $R^9$, $R^{10}$, $R^{11}$, and $R^{12}$ each of which may be the same or different, and are any of a hydrogen atom, an alkyl group having 1 to 4 carbon atoms that may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkyl amino group having 1 to 4 carbon atoms, a dialkyl amino group having 2 to 4 carbon atoms, an acylamino group having 2 to 4 carbon atoms, or a halogen atom; and
   the composition thereof is the following composition formula (I):

$$M^{2+}{}_2 A^{2-}{}_2 B \qquad (I)$$

wherein $M^{2+}$ is an ion of the metal M, $A^{2-}$ is 2,3-pyrazinedicarboxylate dianion, and B is an organic ligand (B) capable of bidentate coordination to the metal ion.

[2] The gas separating material according to [1], wherein the target gas is ethylene or 1,3-butadiene.

[3] The gas separating material according to [1] or [2], wherein the metal M is at least one selected from the group consisting of copper, zinc, and cadmium.

[4] The gas separating material according to [1] or [2], wherein the metal M is copper.

[5] The gas separating material according to any one of [1] to [4], wherein the organic ligand (B) capable of bidentate coordination is pyrazine represented by the general formula (1) wherein all of $R^1$, $R^2$, $R^3$, and $R^4$ are hydrogen atoms.

[6] The gas separating material according to any one of [1] to [4], wherein the organic ligand (B) capable of bidentate coordination is 1,2-di(4-pyridyl)ethane represented by the general formula (2) wherein all of $R^5$, $R^6$, $R^7$, $R^8$, $R^9$, $R^{10}$, $R^{11}$, and $R^{12}$ are hydrogen atoms, and X is —$CH_2$—$CH_2$—, or 1,3-di(4-pyridyl)propane represented by the general formula (2) wherein all of $R^5$, $R^6$, $R^7$, $R^8$, $R^9$, $R^{10}$, $R^{11}$, and $R^{12}$ are hydrogen atoms, and X is —$CH_2$—$CH_2$—$CH_2$—.

[7] The gas separating material according to any one of [1] to [6], wherein the target gas is ethylene, and the hydrocarbon gas having the same number of carbon atoms as the target gas is ethane.

[8] The gas separating material according to any one of [1] to [6], wherein the target gas is 1,3-butadiene, and the hydrocarbon gas having the same number of carbon atoms as the target gas is 1-butene, normal butane, or a mixture thereof.

[9] A method for separating a hydrocarbon gas having a carbon-carbon double bond and having 2 or 4 carbon atoms, the method comprising an adsorption step of bringing a mixed gas containing the target gas defined as a hydrocarbon gas having a carbon-carbon double bond and having 2 or 4 carbon atoms and a hydrocarbon gas having the same number of carbon atoms as the target gas into contact with a separating material to selectively adsorb the target gas on the separating material, and a subsequent regeneration step of desorbing the target gas adsorbed to the separating material from the separating material and collecting the target gas desorbed to separate the hydrocarbon gas having a carbon-carbon double bond and having 2 or 4 carbon atoms from the mixed gas, wherein the separating material is the gas separating material according to any one of [1] to [8].

[10] The separation method according to [9], wherein the target gas is ethylene, and the hydrocarbon gas having the same number of carbon atoms as the target gas is ethane.

[11] The separation method according to [9], wherein the target gas is 1,3-butadiene, and the hydrocarbon gas having the same number of carbon atoms as the target gas is 1-butene, normal butane, or a mixture thereof.

[12] The separation method according to any one of [9] to [11], wherein the separation method is pressure swing adsorption.

[13] The separation method according to any one of [9] to [11], wherein the separation method is temperature swing adsorption.

[14] A separation membrane comprising a porous support and the gas separating material according to any one of [1] to [8] deposited on a surface portion of the porous support.

[15] A separation membrane comprising a polymer material and the gas separating material according to any one of [1] to [8] mixed and dispersed in the polymer material.

[16] A method for separating a hydrocarbon gas having a carbon-carbon double bond and having 2 or 4 carbon atoms, the method comprising a step of bringing a mixed gas containing the target gas defined as a hydrocarbon gas having a carbon-carbon double bond and having 2 or 4 carbon atoms and a hydrocarbon gas having the same number of carbon atoms as the target gas into contact a separation membrane to selectively permeate the target gas through the separation membrane, thereby obtaining a gas with a higher concentration of the target gas than the mixed gas, wherein the separation membrane is the separation membrane according to [14] or [15].

[17] An adsorption sheet comprising the gas separating material according to any one of [1] to [8] and an organic fiber.

[18] The adsorption sheet according to [17], wherein the organic fiber is a cellulose fiber.

[19] The adsorption sheet according to [17] or [18] produced by the wet papermaking method.

Effects of the Invention

The present invention can separate and recover a hydrocarbon gas having a carbon-carbon double bond from a mixed gas containing plural types of hydrocarbons having the same number of carbon atoms, for example, ethylene or 1,3-butadiene, at higher separation performance than conventional art.

The above description should not be regarded as disclosing all embodiments of the present invention and all advantages related to the present invention.

MODE FOR CARRYING OUT THE INVENTION

Representative embodiments of the present invention will be described in detail below, but the present invention is not limited to these embodiments.

<Metal Complex>

A metal complex used for the separating material of the present invention is a metal complex of
2,3-pyrazinedicarboxylic acid;
at least one metal M ion selected from the group consisting of beryllium, magnesium, calcium, strontium, barium, titanium, vanadium, chromium, manganese, iron, ruthenium, cobalt, rhodium, nickel, palladium, platinum, copper, zinc, and cadmium;
an organic ligand (B) capable of bidentate coordination to the metal ion, represented by the following general formula (1):

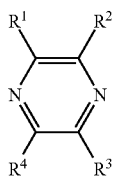

(1)

or the following general formula (2):

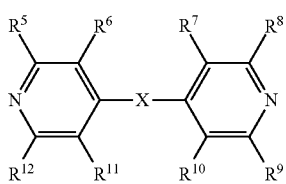

(2)

wherein X is any of —$CH_2$—, —$CH_2$—$CH_2$—, —$CH_2$—$CH_2$—$CH_2$—, —CH=CH—, —C≡C—, —O—, —S—, —S—S—, —N=N—, or —NHCO—, and $R^1$, $R^2$, $R^3$, $R^4$, $R^5$, $R^6$, $R^7$, $R^8$, $R^9$, $R^{10}$, $R^{11}$, and $R^{12}$ each of which may be the same or different, and are any of a hydrogen atom, an alkyl group having 1 to 4 carbon atoms that may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkyl amino group having 1 to 4 carbon atoms, a dialkyl amino group having 2 to 4 carbon atoms, an acylamino group having 2 to 4 carbon atoms, or a halogen atom; and
the composition thereof is the following composition formula (I):

$$M^{2+}_2 A^{2-}_2 B \quad (I)$$

wherein $M^{2+}$ is an ion of the metal M, $A^{2-}$ is 2,3-pyrazinedicarboxylate dianion, and B is an organic ligand (B) capable of bidentate coordination to the metal ion.

A metal complex of the present invention is mainly composed of a metal M, 2,3-pyrazinedicarboxylic acid, and an organic ligand (B) capable of bidentate coordination. A metal complex used for the separating material of the present invention is usually made with a ratio of metal ion:2,3-pyrazinedicarboxylic acid:organic ligand (B) capable of bidentate coordination=2 mol:2 mol:1 mol, but deviations from the ratio are acceptable as long as the effects of the present invention are obtained.

Figure 1:
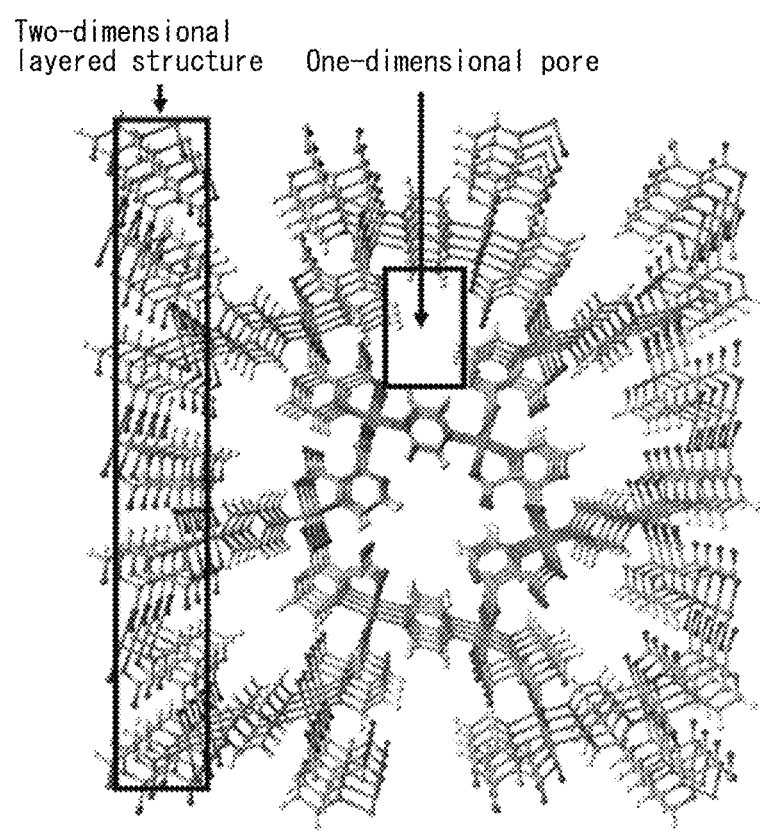
FIG. 1 is a structural diagram of a metal complex: [$Cu_2$(pydc)$_2$(pyz)] of copper, 2,3-pyrazinedicarboxylic acid, and pyrazine.

As a preferable example of a metal complex formed from at least one metal selected from a metal M, 2,3-pyrazinedicarboxylic acid, and an organic ligand (B) capable of bidentate coordination, the structure of a metal complex of a bivalent copper cation, a 2,3-pyrazinedicarboxylate dianion, and pyrazine represented by the following composition formula (II):

$$[(Cu^{2+})_2(pydc^{2-})_2(pyz)] \quad (II)$$

is schematically shown in FIG. 1. The "pydc" represents 2,3-pyrazinedicarboxylic acid, and the "pyz" represents pyrazine. In this metal complex, a copper ion and a 2,3-pyrazinedicarboxylate dianion build a two-dimensional sheet-like (layered) structure, and an organic ligand (B) capable of bidentate coordination is cross-linked to the sheet-like structures to form a one-dimensional pore with a pore diameter of approximately 3 to 4 Å. By utilizing this relatively smaller pore diameter and by recognizing gas molecules by the difference in their sizes, molecules with relatively smaller sizes can be selectively adsorbed. More specifically, for example, ethylene from hydrocarbons having 2 carbon atoms, and 1,3-butadiene from hydrocarbons having 4 carbon atoms, can be selectively adsorbed.

(Metal M)

A metal M constituting the metal complex of the present invention may be selected from beryllium, magnesium, calcium, strontium, barium, titanium, vanadium, chromium, manganese, iron, ruthenium, cobalt, rhodium, nickel, palladium, platinum, copper, zinc, and cadmium. Of these, copper, zinc, and cadmium are preferable, and copper is most preferable in terms of the flexibility of a metal complex formed.

(Organic Ligand (B) Capable of Bidentate Coordination)

An organic ligand (B) capable of bidentate coordination to the metal ion used for the present invention is represented by the following general formula (1) or (2):

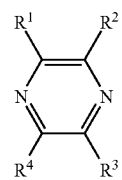

(1)

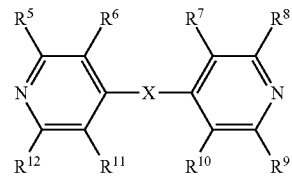

(2)

wherein X is any of —$CH_2$—, —$CH_2$—$CH_2$—, —$CH_2$—$CH_2$—$CH_2$—, —CH=CH—, —C≡C—, —O—, —S—, —S—S—, —N=N—, or —NHCO—, and $R^1$, $R^2$, $R^3$, $R^4$, $R^5$, $R^6$, $R^7$, $R^8$, $R^9$, $R^{10}$, $R^{11}$, and $R^{12}$ each of which may be the same or different, and are any of a hydrogen atom, an alkyl group having 1 to 4 carbon atoms that may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkyl amino group having 1 to 4 carbon atoms, a dialkyl amino group having 2 to 4 carbon atoms, an acylamino group having 2 to 4 carbon atoms, or a halogen atom.

An organic ligand capable of bidentate coordination herein refers to a ligand having two coordination sites to a metal via lone pairs.

X is any of —$CH_2$—, —$CH_2$—$CH_2$—, —$CH_2$—$CH_2$—$CH_2$—, —CH=CH—, —C≡C—, —O—, —S—, —S—S—, —N=N—, or —NHCO—. By selecting X according to the target gas, the size of a one-dimensional pore of a metal complex can be adjusted to achieve the selective adsorption of the target gas. Of these, —$CH_2$—$CH_2$—, —$CH_2$—$CH_2$—$CH_2$—, and —S—S— are preferable, and —$CH_2$—$CH_2$—$CH_2$— is more preferable since they tend to form a one-dimensional pore with a size suitable for the selective adsorption of the target gas of the present invention.

Examples of the alkyl group having 1 to 4 carbon atoms include an alkyl group having a straight chain or branched chain, such as a methyl group, an ethyl group, an n-propyl group, an isopropyl group, an n-butyl group, an isobutyl group, and a tert-butyl group. Examples of the substituent which may be included in the alkyl group include an alkoxy group (methoxy group, ethoxy group, n-propoxy group, isopropoxy group, n-butoxy group, isobutoxy group, tert-butoxy group, and the like), an amino group, a monoalkyl amino group (methylamino group, and the like), a dialkyl amino group (dimethylamino group, and the like), a formyl group, an epoxy group, an acyloxy group (acetoxy group, n-propanoyloxy group, n-butanoyloxy group, pivaloyloxy group, benzoyloxy group, and the like), an alkoxycarbonyl group (methoxycarbonyl group, ethoxycarbonyl group, n-butoxycarbonyl group, and the like), and a carboxylic anhydride group (—CO—O—CO—R group) (R is an alkyl group having 1 to 4 carbon atoms). When an alkyl group has a substituent, the number of substituents is preferably 1 to 3, and more preferably 1.

Examples of the alkenyl group having 2 to 4 carbon atoms include a vinyl group, an allyl group, a 1-propenyl group, and a butenyl group.

Examples of the alkoxy group having 1 to 4 carbon atoms includes a methoxy group, an ethoxy group, an n-propoxy group, an isopropoxy group, an n-butoxy group, an isobutoxy group, and a tert-butoxy group.

Examples of the acyloxy group having 2 to 10 carbon atoms include an acetoxy group, an n-propanoyloxy group, an n-butanoyloxy group, a pivaloyloxy group, and a benzoyloxy group.

Examples of the alkoxycarbonyl group having 2 to 4 carbon atoms include a methoxycarbonyl group, an ethoxycarbonyl group, and an n-butoxycarbonyl group.

Examples of the monoalkyl amino group having 1 to 4 carbon atoms include a methylamino group. Examples of the dialkyl amino group having 2 to 4 carbon atoms include a dimethylamino group. Examples of the acylamino group having 2 to 4 carbon atoms include an acetylamino group.

Examples of the halogen atom include fluorine, chlorine, bromine, and iodine atoms.

It is preferable that $R^1$, $R^2$, $R^3$, $R^4$, $R^5$, $R^6$, $R^7$, $R^8$, $R^9$, $R^{10}$, $R^{11}$, and $R^{12}$ be independently a hydrogen atom or an unsubstituted alkyl group having 1 to 4 carbon atoms, in view of the amount of gas adsorption, and it is more preferable that all of them be hydrogen atoms.

An organic ligand (B) capable of bidentate coordination is preferably pyrazine in which all of $R^1$, $R^2$, $R^3$, and $R^4$ are hydrogen atoms, 1,2-di(4-pyridyl)ethane in which all of $R^5$, $R^6$, $R^7$, $R^8$, $R^9$, $R^{10}$, $R^{11}$, and $R^{12}$ are hydrogen atoms and X is —$CH_2$—$CH_2$—, or 1,3-di(4-pyridyl)propane in which all of $R^5$, $R^6$, $R^7$, $R^8$, $R^9$, $R^{10}$, $R^{11}$, and $R^{12}$ are hydrogen atoms and X is —$CH_2$—$CH_2$—$CH_2$—.

<Separating Material>
(Method for Producing Separating Material Containing Metal Complex)

A metal complex of the present invention can be produced by reacting 2,3-pyrazinedicarboxylic acid, a salt of a metal M, and an organic ligand (B) capable of bidentate coordination with an ion of the metal M in a solvent under normal pressure for several hours to several days to precipitate a crystal insoluble in the solvent, followed by separation, washing and further recovery of the crystal. For example, a metal complex of the present invention can be obtained by mixing an aqueous solution or aqueous-organic solvent solution of the metal salt with an organic solvent solution containing 2,3-pyrazinedicarboxylic acid and an organic ligand (B) capable of bidentate coordination under normal pressure, and reacting the mixture.

When a metal complex of the present invention is produced, a salt of the metal M may be used. As the metal salt, a single metal salt is preferably used, but a mixture of two or more metal salts may be used. As these metal salts, an organic salt, such as acetate, and an inorganic acid salt, such as perchlorate, hydrochloride, hydrobromide, sulfate, nitrate, or carbonate, may be used.

A mixing ratio of 2,3-pyrazinedicarboxylic acid to an organic ligand (B) capable of bidentate coordination when a metal complex is produced is preferably within a range of a molar ratio of 2,3-pyrazinedicarboxylic acid:organic ligand (B) capable of bidentate coordination=1:5 to 5:1, and more preferably within a range of a molar ratio of 1:3 to 3:1. Even when reaction is carried out outside this range, the target metal complex can be obtained; however, the yield may decrease and a side reaction may also increase.

A mixing ratio of a metal salt to an organic ligand (B) capable of bidentate coordination when a metal complex is produced is preferably within a range of a molar ratio of metal salt:organic ligand (B) capable of bidentate coordination=5:1 to 1:5, and more preferably within a range of a molar ratio of 3:1 to 1:3. Outside this range, the yield of the target metal complex decreases, and it is difficult to purify the resulting metal complex due to the residual unreacted raw materials.

A mixing ratio of a metal salt, 2,3-pyrazinedicarboxylic acid and an organic ligand (B) capable of bidentate coordination when a metal complex is produced may be different from a composition ratio in the metal complex to be produced. Since a metal complex tends to form a thermodynamically stable structure under its production conditions, a ratio of a metal salt, dicarboxylic acid, and an organic ligand capable of bidentate coordination can be controlled by the concentration of each raw material, reaction temperature, reaction time, pH, and the like.

A molar concentration of a metal salt in a solution for the production of a metal complex is preferably 0.005 to 5.0 mol/L, and more preferably 0.01 to 2.0 mol/L. Although the target metal complex can be obtained even when reaction is carried out at a lower concentration, such concentration is not preferable since the yield decreases. At a higher concentration, an unreacted metal salt remains, and it may be difficult to purify the resulting metal complex.

The molar concentration of 2,3-pyrazinedicarboxylic acid in a solution for the production of a metal complex is preferably 0.001 to 5.0 mol/L, and more preferably 0.005 to 2.0 mol/L. Although the target metal complex can be obtained even when reaction is carried out at a lower concentration, such concentration is not preferable since the yield decreases. At a higher concentration, the solubility may decrease, and reaction may not proceed smoothly.

The molar concentration of an organic ligand (B) capable of bidentate coordination in a solvent for the production of a metal complex is preferably 0.001 to 5.0 mol/L, and more preferably 0.005 to 2.0 mol/L. Although the target metal complex can be obtained even when reaction is carried out at a lower concentration, such concentration is not preferable because the yield decreases. At a higher concentration, the solubility may decrease, and reaction may not smoothly proceed.

As a solvent used for the production of a metal complex, an organic solvent, water, or a mixed solvent thereof may be used. Specifically, methanol, ethanol, propanol, diethyl ether, dimethoxyethane, tetrahydrofuran (THF), hexane, cyclohexane, heptane, benzene, toluene, methylene chloride, chloroform, acetone, ethyl acetate, acetonitrile, N,N-dimethylformamide (DMF), N,N-diethylformamide, dimethyl sulfoxide (DMSO), water, or a mixed solvent thereof may be used. The solvent used is preferably a polar solvent, such as water, methanol, ethanol, tetrahydrofuran, acetone, acetonitrile, N,N-dimethylformamide, N,N-diethylformamide, or dimethyl sulfoxide, and particularly preferably water and ethanol. An acid or a base may be added to the solvent to adjust to the pH which is suitable for formation of a complex.

The reaction temperature is preferably −20° C. to 150° C., and more preferably 0° C. to 120° C. The reaction time is preferably 1 to 48 hours, and more preferably 2 to 24 hours.

Completion of reaction can be confirmed by determining the remaining amount of raw materials by gas chromatography or high-performance liquid chromatography. After completion of the reaction, the obtained mixed solution is subjected to suction filtration to collect a precipitate, which is washed with a solvent and then vacuum-dried, for example, at about 60 to 100° C. for several hours, thereby making it possible to obtain a metal complex of the present invention. A highly crystalline metal complex has a high purity and excellent adsorption performance. The crystallinity can be enhanced by adjustment to a suitable pH using an acid or a base.

A metal complex is generally used as a molded separating material. A separating material containing a metal complex is used as, for example, a random packing molded into a bead, ring, strand, or tablet, or as a regular structure, for example, a regular packing, honeycomb body, or monolith.

<Method for Separating Hydrocarbon Gas>

In a method for separating a hydrocarbon gas according to one embodiment of the present invention, a mixed gas containing the target hydrocarbon gas, which is to be separated, is brought into contact with the separating material of the present invention, the target hydrocarbon gas is selectively adsorbed to the separating material, and then the target hydrocarbon gas adsorbed onto the separating material is desorbed from the separating material to collect the target hydrocarbon gas thus desorbed.

Examples of the target hydrocarbon gas include a hydrocarbon gas having a carbon-carbon double bond and having 2 to 5 carbon atoms, such as, for example, ethylene, propylene, 1-butene, 2-butene, 1,3-butadiene, 1-pentene, 2-pentene, and 1,3-pentadiene. A separating material of the present invention can be used advantageously for hydrocarbon gases having a carbon-carbon double bond and having 2 or 4 carbon atoms in some embodiments, and can be used advantageously for ethylene, propylene, 1,3-butadiene, and 1,3-pentadiene in other embodiments. A separating material of the present invention shows high selectivity particularly for ethylene and 1,3-butadiene, and can separate and recover these hydrocarbon gases at high separation performance.

When the target hydrocarbon gas is 1,3-butadiene, there is no particular limitation on other gases contained in the mixed gas. A separating material of the present invention is particularly effective when 1,3-butadiene is separated from a mixed gas containing a hydrocarbon having 4 carbon atoms, including isobutene, 1-butene, 2-butene, normal butane, and isobutane, particularly 1-butene, normal butane, or a mixture thereof, as other gases, which are difficult to be separated by using the conventional separating materials since the boiling points are close to that of 1,3-butadiene.

When the target hydrocarbon gas is ethylene, there is no particular limitation on other gases contained in mixed gas. A separating material of the present invention is particularly effective when ethylene is separated from a mixed gas containing ethane, the boiling point of which is close to that of ethylene, as other gases.

In contact of a mixed gas with a separating material, it is desirable to select temperature and pressure conditions where only the target hydrocarbon gas is effectively adsorbed to the separating material.

The separation method comprises an adsorption step of bringing a mixed gas into contact with a separating material of the present invention under conditions where the target hydrocarbon gas can be adsorbed to the separating material. The adsorption pressure and adsorption temperature, which are conditions where the target hydrocarbon gas can be adsorbed to the separating material, can be suitably set depending on the type of a substance to be adsorbed, the design of an apparatus, purity required for a product gas, and the like.

The separation method may be a pressure swing adsorption method or a temperature swing adsorption method.

When the separation method is a pressure swing adsorption method, the method comprises a step (adsorption step) of bringing a mixed gas containing the target gas into contact with a separating material to allow only the target gas to be selectively adsorbed to the separating material, and a step (regeneration step) of reducing the pressure from the adsorption pressure to a pressure at which the adsorbed gas can be desorbed from the separating material. The desorption pressure can be suitably set depending on the type of a substance to be adsorbed, the design of an apparatus, purity required for a product gas, and the like. For example, the desorption pressure is preferably 0.05 to 50 kPa, and more preferably 0.05 to 30 kPa.

A method for separating 1,3-butadiene using a separating material of the present invention when a mixed gas contains 1,3-butadiene as the target hydrocarbon gas and hydrocarbons having 4 carbon atoms, which is the same as for 1,3-butadiene, as other gases, will be described.

The proportion of 1,3-butadiene in a mixed gas to be subjected to separation can be various values, and this proportion greatly depends on the source of the mixed gas. In addition to 1,3-butadiene, the mixed gas contains at least a hydrocarbon, such as isobutene, 1-butene, 2-butene, normal butane, and isobutane, and may further contain other hydrocarbons. The mixed gas preferably contains 10 to 99% by volume of 1,3-butadiene for the total of the volume percent of 1,3-butadiene and other hydrocarbon(s) in the mixed gas. More preferably, the proportion of 1,3-butadiene is 20 to 60% by volume.

In the case of the pressure swing adsorption method, the adsorption pressure as a partial pressure of 1,3-butadiene in the mixed gas is preferably 10 to 200 kPa, and more preferably 30 to 100 kPa. The desorption pressure is preferably 0.05 to 50 kPa. The temperature is preferably −10° C. to 100° C. In the case of the temperature swing adsorption method, the adsorption temperature is preferably 0° C. to 50° C. The desorption temperature is preferably 50° C. to 150° C. The pressure is preferably 10 to 300 kPa.

Next, a method for separating ethylene using a separating material of the present invention when a mixed gas contains ethylene as the target hydrocarbon gas and ethane as other gases will be described.

The mixed gas preferably contains 10 to 99% by volume of ethylene for the total of the volume percent of ethylene and other hydrocarbon(s) in the mixed gas. More preferably, the proportion of ethylene is 20 to 80% by volume.

In the case of the pressure swing adsorption method, the adsorption pressure as a partial pressure of ethylene is preferably 200 to 2,000 kPa, and more preferably 500 to 1,000 kPa. The desorption pressure is preferably 5 to 100 kPa. The temperature is preferably −80° C. to 5° C. In the case of the temperature swing adsorption method, the adsorption temperature is preferably 0° C. to 50° C. The desorption temperature is preferably 50° C. to 150° C. The pressure is preferably 10 to 300 kPa.

Figure 2:
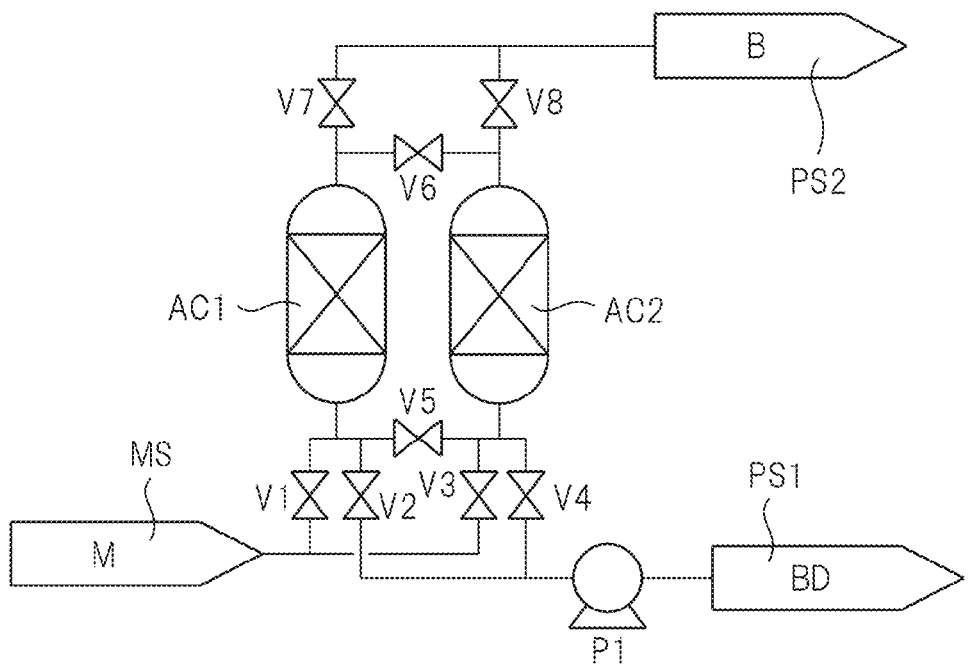
FIG. 2 is a schematic diagram of an apparatus that recovers the target gas from a mixed gas by pressure swing adsorption.

The pressure swing adsorption method in which the target gas is 1,3-butadiene will be specifically described with reference to FIG. 2. Adsorption columns AC1 and AC2 are filled with a separating material of the present invention. A mixed gas (M) containing 1,3-butadiene, butene, butane, and the like is pressurized to about 0.3 MPa by a compressor and supplied to adsorption column AC1 filled with the separating material through valve V1 (abbreviated to "V1", the same shall apply hereinafter) from mixed gas storage tank MS. As is apparent from FIG. 10, when a partial pressure of 1,3-butadiene exceeds 10 kPa, 1,3-butadiene is selectively adsorbed onto the separating material in adsorption column AC1 (adsorption step). Meanwhile, butanes and butenes are not adsorbed, and discharged from adsorption column AC1. As a result, the gas (B) in which butanes and butenes are concentrated is sent to product storage tank PS2 through V7. Next, adsorption column AC1 is suctioned by vacuum pump P1 in the state where V1, V5, V6, and V7 are closed and V2 is opened. As is apparent from FIG. 10, when the pressure is decreased to below 2 kPa, the gas (BD) containing 1,3-butadiene as a main component adsorbed onto the separating material in adsorption column AC1 is desorbed and sent to product storage tank PS1 (desorption step). In the same manner, the adsorption step is completed for adsorption column AC2. After the desorption step of adsorption column AC1 is carried out for a prescribed time, V1, V2, V3, V4, V7, and V8 are closed, and V5 and V6 are opened, and then the mixed gas remaining in adsorption column AC2 is recovered to adsorption column AC1 employing a pressure difference between adsorption column AC1 and adsorption column AC2 (pressure equalizing step). Each product gas can be efficiently obtained without lessening its purity by carrying out the pressure equalizing step. Next, while adsorption column AC2 is suctioned by vacuum pump P1 in the state where V2, V3, V5, V6, and V8 are closed and V4 is opened, the adsorbed gas (BD) containing 1,3-butadiene as a main component is desorbed and sent to product storage tank PS1. To adsorption column AC1, a mixed gas (M) containing 1,3-butadiene is supplied in the state where V2, V3, V5, V6, and V8 are closed and V1 and V7 are opened, and then the adsorption step is carried out again. In adsorption column AC1 and adsorption column AC2, adsorbing and desorbing operations are alternately repeated in a suitably determined cycle by a timer or the like to continuously produce each product gas.

When the target gas is ethylene and other gases are ethane, ethylene can be separated, as with 1,3-butadiene, for example, by setting the adsorption pressure at 500 kPa or more and the desorption pressure at 50 kPa or less.

When the separation method is the temperature swing adsorption method, the method comprises a step (adsorption step) of bringing a mixed gas containing the target hydrocarbon gas into contact with a separating material to allow only the target hydrocarbon gas to be selectively adsorbed to the separating material, and a step (regeneration step) of raising the temperature from the adsorption temperature to a temperature at which the adsorbed gas can be desorbed from the separating material. The desorption temperature can be suitably set depending on the type of a substance to be adsorbed, the design of an apparatus, production efficiency, and the like. For example, in the case of separation of 1,3-butadiene, the desorption temperature is preferably 0 to 200° C., and more preferably 20° C. to 150° C. In the case of separation of ethylene, the desorption temperature is preferably 20° C. to 200° C., and more preferably 30° C. to 150° C.

When the separation method is the pressure swing adsorption method or the temperature swing adsorption method, a step (adsorption step) of bringing a mixed gas into contact with a separating material, and a step (regeneration step) of changing the pressure or temperature to a pressure or temperature at which the target hydrocarbon gas can be desorbed from the separating material can be suitably repeated.

<Separation Membrane>

Membrane separation is also included in separation methods other than above mentioned methods. A separation membrane can be obtained by depositing a metal complex to a surface portion of a porous support, for example, by crystal growth. As a material of a porous support, a composition composed of silica or alumina, such as alumina, silica, mullite, or cordierite, and other components; a porous sintered metal; a porous glass, and the like may be suitably used. Ceramics including other oxides, such as zirconia and magnesia, and carbides and nitrides, such as silicon carbide and silicon nitride, gypsum, cement, and the like, or a mixture thereof may also be used. The porosity of a porous support is typically about 30 to 80%, preferably 35 to 70%, and most preferably 40 to 60%. Too small porosity is not preferred since the permeability of a fluid, such as gas, deteriorates, while too large porosity is not preferred since the strength of a support decreases. The pore diameter of a porous support is typically 10 to 10,000 nm, and preferably 100 to 10,000 nm. A separation membrane obtained by the crystal growth of a metal complex on a surface portion of a porous support is obtainable by impregnating a porous support in a solution containing a raw material of a metal complex, optionally followed by heating.

A separation membrane can also be obtained by kneading a metal complex of the present invention with a polymer material to disperse the metal complex into the polymer material, and forming the mixture into a film. Examples of the polymer material include polymer materials for gas separation membrane, such as polyvinyl acetate, polyimide and polydimethylsiloxane.

In the membrane separation, when mixed gas containing the target hydrocarbon gas, for example, 1,3-butadiene or ethylene is brought into contact with the separation membrane, the permeability P of each gas in the mixed gas is represented by the product of the solubility S of each gas in the membrane by the diffusion coefficient D thereof in the membrane. Since a gas having higher permeability P selectively permeates through the membrane, such a gas can be separated and recovered from the mixed gas. Therefore, by forming a membrane of a metal complex of the present invention having high selectivity of hydrocarbon gases having a carbon-carbon double bond and having 2 to 5 carbon atoms, particularly hydrocarbon gases having a carbon-carbon double bond and having 2 or 4 carbon atoms, for example, 1,3-butadiene or ethylene, a membrane enabling selective permeation of such hydrocarbon gases can be obtained. For example, when a mixed gas is passed through an inner tube of a double tube, the double tube equipped with a gas impermeable outer tube and the inner tube composed of a separation membrane, the above mentioned hydrocarbon gas selectively permeates through the inner tube and concentrated between the outer tube and the inner tube, and thus the target hydrocarbon gas can be separated by collecting the gas.

<Adsorption Sheet>

An adsorption sheet of the present invention contains a metal complex, which is a gas separating material of the present invention, and an organic fiber. The form of a metal complex used for the adsorption sheet includes various forms, such as a particle, powder, fiber, film, and plate, and is preferably powder. A metal complex with a mean particle diameter of 1 μm to 500 μm (more preferably 5 μm to 100 μm) can be suitably used. "Mean particle diameter" in the present invention refers to a diameter at a number cumulative frequency of 50% (median diameter), and can be measured, for example, with a laser diffraction/scattering particle size analyzer.

The amount of a metal complex contained in an adsorption sheet of the present invention is preferably 50% by weight to 90% by weight. By considering the adsorption performance, the productivity of an adsorption sheet, elimination of a metal complex, and the like, the content of a metal complex is more preferably 60% by weight to 80% by weight. When the content of a metal complex is less than 50% by weight, the adsorption efficiency of gas per unit mass tends to decrease, while when the content exceeds 90% by weight, the productivity of an adsorption sheet tends to decrease or elimination of a metal complex tends to occur frequently.

(Organic Fiber)

An organic fiber is a component that functions as a carrier supporting a metal complex, and is preferably a pulp fiber. In terms of highly supporting a metal complex on an adsorption sheet, an organic fiber is desirably fibrillated. Pulp refers to a separated and processed state to be used for papermaking.

Examples of the organic fiber include cellulose fiber, polyester, vinylon, polypropylene, polyamide, rayon, acrylic fiber, polylactic acid fiber, polybenzimidazole, polybenzoxazole, polyimide, polyamide-imide, and polyether ketone. Usually, a cellulose fiber (paper) is preferable in terms of a balance between easy handling and cost, and the like. When thermostability is required for an adsorption sheet, more preferably a fiber produced from a wholly aromatic polyamide, such as aramid and meta-aramid, polybenzimidazole, polybenzoxazole, polyimide, polyamide-imide, or polyether ketone is used. The above mentioned organic fibers may be used alone or in a mixture of two or more fibers.

The amount of an organic fiber contained in an adsorption sheet is preferably 5% by weight to 20% by weight. When the content of an organic fiber is less than 5% by weight, the capacity of supporting a metal complex tends to be insufficient, while the content exceeds 20% by weight, the amount of a metal complex contained in an adsorption sheet becomes relatively small, and thus it may be difficult to obtain a sufficient adsorption effect. The amount is more preferably 10% by weight to 20% by weight, and still more preferably 15% by weight to 20% by weight.

(Other Components)

In an adsorption sheet, an organic binder may be used as needed as a binder to support a metal complex on an organic fiber. There is no particular limitation on the organic binder as long as the binder can support a metal complex on an adsorption sheet at a high ratio when the adsorption sheet is produced. Specific examples of the organic binder include polyvinyl alcohol (PVA), starch, polyacrylonitrile, methylcellulose, and carboxymethylcellulose.

The amount of an organic binder is preferably 5% by weight to 30% by weight for a total of 100% by weight of the components of an adsorption sheet. The amount is more preferably 5% by weight to 10% by weight, and still more preferably 5% by weight to 7% by weight. When the amount of an organic binder is less than 5% by weight, the fixity of a metal complex to an organic fiber or the connectivity between organic fibers tends to be poor, while the amount exceeds 30% by weight, the amount of a metal complex in an adsorption sheet becomes relatively small, and thus it may be difficult to obtain a sufficient adsorption effect.

In preferable embodiments, an adsorption sheet of the present invention may contain additives other than a metal complex, an organic fiber, and an organic binder as needed. Additives, for example, include a glass fiber which is intended to improve the mechanical strength of an adsorption sheet, a polymer coagulant, and a pigment. The amount of these components is preferably 0% by weight to 10% by weight for a total of 100% by weight of the components of an adsorption sheet. The amount is more preferably 3% by weight to 7% by weight.

There is no particular limitation on a method for producing an adsorption sheet of the present invention. For example, the method includes wet papermaking method. When a sheet-like object is produced by the wet papermaking method, first, a metal complex, an organic fiber, and other components, such as an optional organic binder, are dispersed into water at a predetermined compounding ratio to prepare a dispersed slurry. The concentration of each component in the dispersed slurry may be suitably adjusted so that the content in an adsorption sheet is within the above mentioned range.

Next, the dispersed slurry obtained is subjected to papermaking with a papermaking machine to obtain a sheet-like object, and then the object is dehydrated and dried to obtain an adsorption sheet. There is also no limitation on a method for dehydration and drying, and any of the conventional publicly known methods, such as pressure dehydration by passing a sheet-like object between a pair of rolls, solar drying, and spraying of hot air to a sheet-like object after dehydration, can be used.

The thickness of an adsorption sheet of the present invention is preferably 0.01 mm to 2 mm. The thickness is more preferably 0.1 mm to 0.5 mm, and still more preferably 0.1 mm to 0.3 mm. When the thickness of an adsorption sheet is too small, it is difficult to increase the amount of a supported metal complex, while the thickness is too large, the processability of an adsorption sheet into an adsorption element in a gas separation apparatus or the like may be decreased. The basis weight of an adsorption sheet of the present invention is preferably 50 to 200 $g/m^2$. The basis weight is more preferably 130 to 170 $g/m^2$. When the basis weight is too small, the adsorption sheet structure is loose and the amount of a supported metal complex decreases, and thus it may be difficult to exert sufficient adsorption performance, and when the basis weight is too large, an adsorption sheet becomes thicker, and problems, such as a fracture, when the sheet is processed into an adsorption element may occur.

An adsorption sheet of the present invention has excellent separation performance that separates a specific gas from a mixed gas, since a metal complex can selectively adsorb only a specific type of gas while its structure or size is changed and the adsorption sheet has a metal complex that can adsorb and desorb a specific gas by changes in pressure. Since the components of the adsorption sheet is relatively flexible and can keep up with structural changes of a metal complex, excellent performance that a metal complex has can be exerted also in the adsorption sheet. Therefore, an adsorption sheet of the present invention is preferably used as, for example, an adsorption sheet constituting an adsorption element in a gas separation apparatus using pressure swing adsorption.

EXAMPLES

The present invention will be specifically described below by way of Examples, but the present invention is not limited thereto. Analysis and evaluation in the following Examples and Comparative Examples were carried out as follows.
(1) Measurement of Adsorption-Desorption Isotherm Measurement was carried out by a volumetric method using a high-pressure gas adsorption apparatus. Prior to measurement, samples were dried at 150° C. under 50 Pa for 6 hours to remove adsorbed water, and the like. Details of analysis conditions are shown below.
<Analysis Conditions>
Apparatus: BELSORP-HP and BELSORP-18HT, manufactured by BEL Japan, Inc.
Equilibrium waiting time: 500 seconds Example 1

Synthesis of Porous Metal Complex (1):
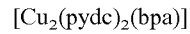

Copper nitrate trihydrate (1.23 g, 5.0 mmol, 1.0 eq.), pyrazine (4.05 g, 50.0 mmol, 10.0 eq.), and pure water (100 mL) were added to a recovery flask (500 mL) to be mixed. To a blue transparent solution obtained, a mixed solution of a 2,3-pyrazinedicarboxylic acid (0.84 g, 5.0 mmol, 1.0 eq.) solution (80 mL) and a 1N sodium hydroxide solution (20 mL) were added dropwise. After the mixed solution was stirred at room temperature (25° C.) for 2 hours, a blue solid obtained was filtered with a Kiriyama-rohto (registered trademark), washed with pure water and methanol in this order, and dried to obtain a blue powder (porous metal complex (1)) (yield: 1.32 g).

Example 2

Synthesis of Porous Metal Complex (2):
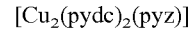

Copper perchlorate hexahydrate (0.74 g, 2.0 mmol, 1.0 eq.), pure water (100 mL), and ethanol (100 mL) were added to a recovery flask (1000 mL) to be mixed. To a blue transparent solution obtained, a mixed solution of 2,3-pyrazinedicarboxylic acid (0.34 g, 2.0 mmol, 1.0 eq.), 1,3-di(4-pyridyl)propane (0.20 g, 1.0 mmol, 0.5 eq.), 1N sodium hydroxide solution (4 mL), pure water (96 mL), and ethanol (100 mL) was added dropwise. After the mixed solution was stirred at room temperature (25° C.) for 16 hours, a blue solid obtained was filtered with a Kiriyama-rohto (registered trademark), washed with pure water and ethanol in this order, and dried to obtain a blue powder (porous metal complex (2)) (yield: 0.71 g).

Example 3

Synthesis of Porous Metal Complex (3):
$[Cu_2(pydc)_2(bpa)]$

Copper perchlorate hexahydrate (0.75 g, 2.0 mmol, 1.0 eq.), pure water (100 mL), and ethanol (100 mL) were added to a recovery flask (1000 mL) to be mixed. To a blue transparent solution obtained, a mixed solution of 2,3-pyrazinedicarboxylic acid (0.33 g, 2.0 mmol, 1.0 eq.), 1,2-di(4-pyridyl)ethane (0.18 g, 1.0 mmol, 0.5 eq.), 1N sodium hydroxide solution (4 mL), pure water (96 mL), and ethanol (100 mL) was added dropwise. After the mixed solution was stirred at room temperature (25° C.) for 16 hours, a blue solid obtained was filtered with a Kiriyama-rohto (registered trademark), washed with pure water and ethanol in this order, and dried to obtain a blue powder (porous metal complex (3)) (yield: 0.54 g).

Example 4

Production of Adsorption Sheet

Figure 3:
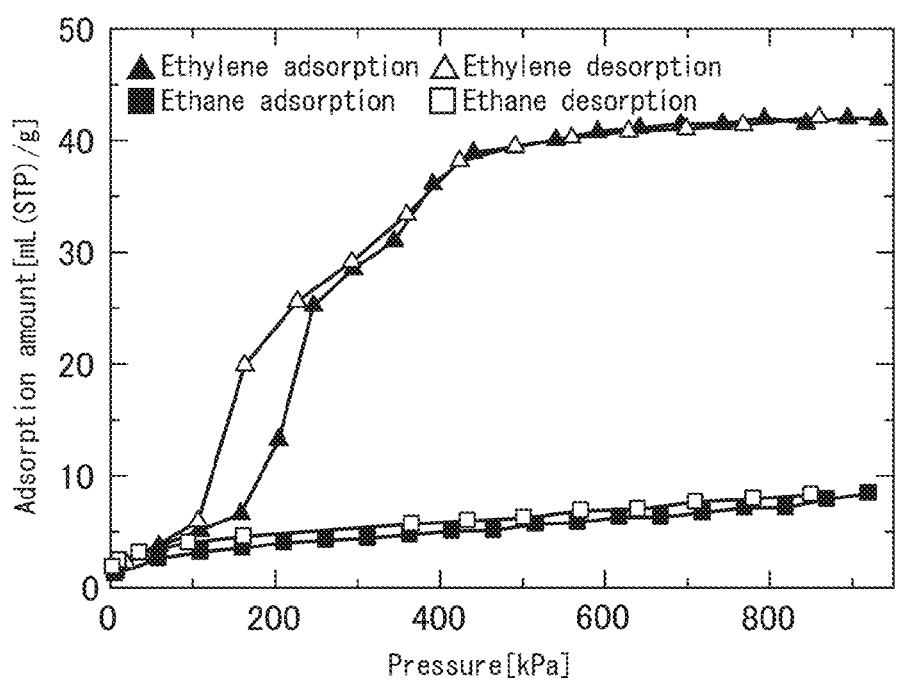
FIG. 3 illustrates an adsorption-desorption isotherm of ethylene and ethane at 0° C. for the metal complex obtained in Example 1.
Figure 4:
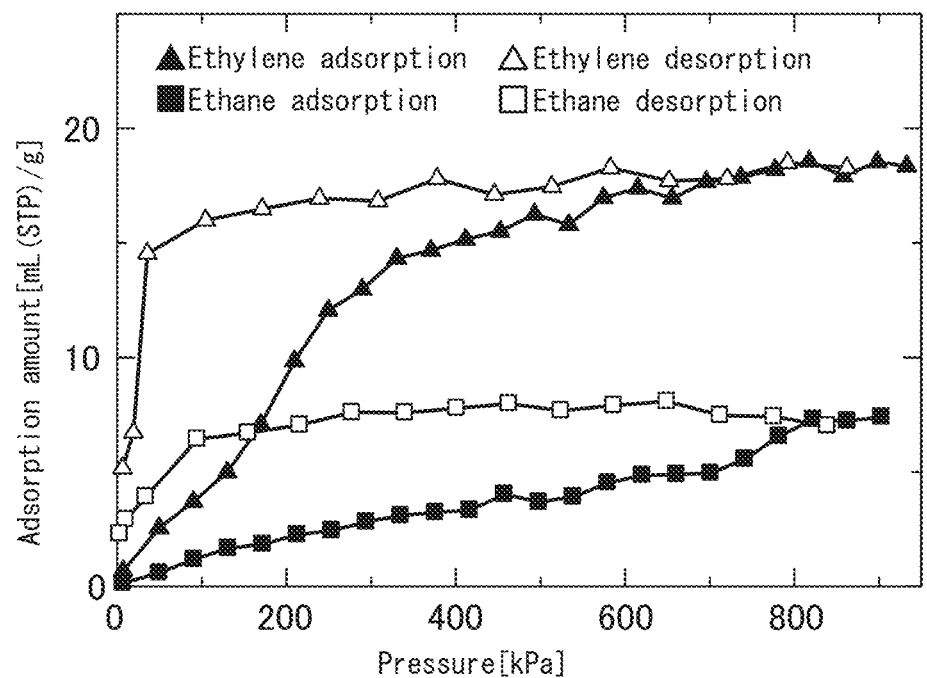
FIG. 4 illustrates an adsorption-desorption isotherm of ethylene and ethane at 0° C. for the metal complex obtained in Example 2.
Figure 5:
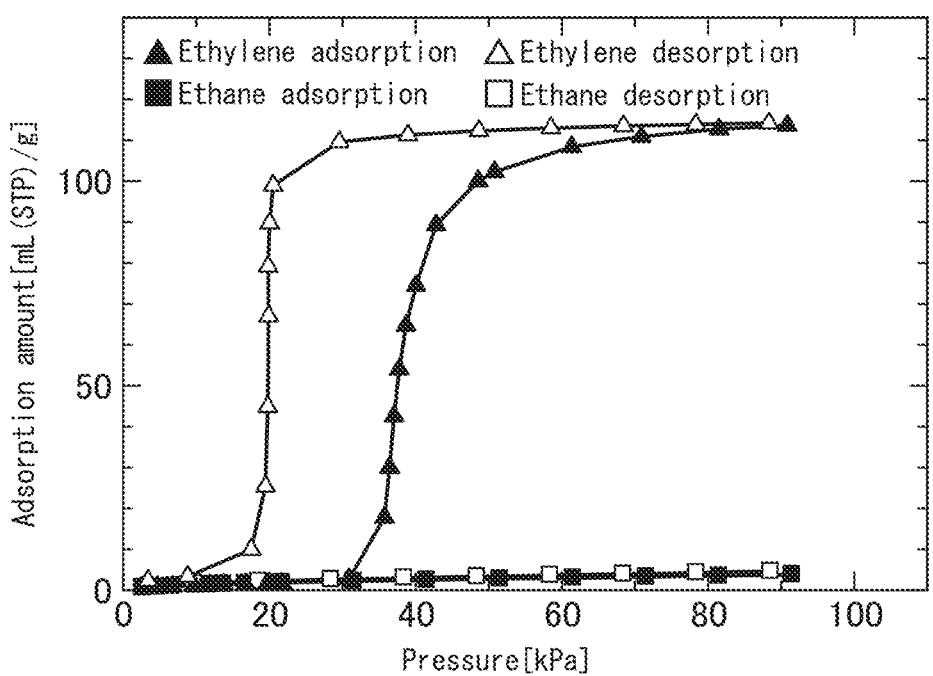
FIG. 5 illustrates an adsorption-desorption isotherm of ethylene and ethane at −78° C. for the metal complex obtained in Example 3.

By using a wet papermaking apparatus, an adsorption sheet (1), which is a sheet-like formed article with a thickness of about 0.26 mm and a basis weight of about 150 g/m², was produced so that the composition in the adsorption sheet was porous metal complex (1) of 70% by weight, pulp cellulose as an organic fiber of 20% by weight, PVA as an organic binder of 5% by weight, and glass fiber as an inorganic fiber of 5% by weight.
<Adsorption Isotherm 1>
For the porous metal complex (1) obtained in Example 1, an adsorption-desorption isotherm of ethylene and ethane at 0° C. was measured. The results are shown in FIG. 3.
<Adsorption Isotherm 2>
For the porous metal complex (2) obtained in Example 2, an adsorption-desorption isotherm of ethylene and ethane at 0° C. was measured. The results are shown in FIG. 4.
<Adsorption Isotherm 3>
For the porous metal complex (3) obtained in Example 3, an adsorption-desorption isotherm of ethylene and ethane at −78° C. was measured. The results are shown in FIG. 5.

Comparative Example 1

Figure 6:
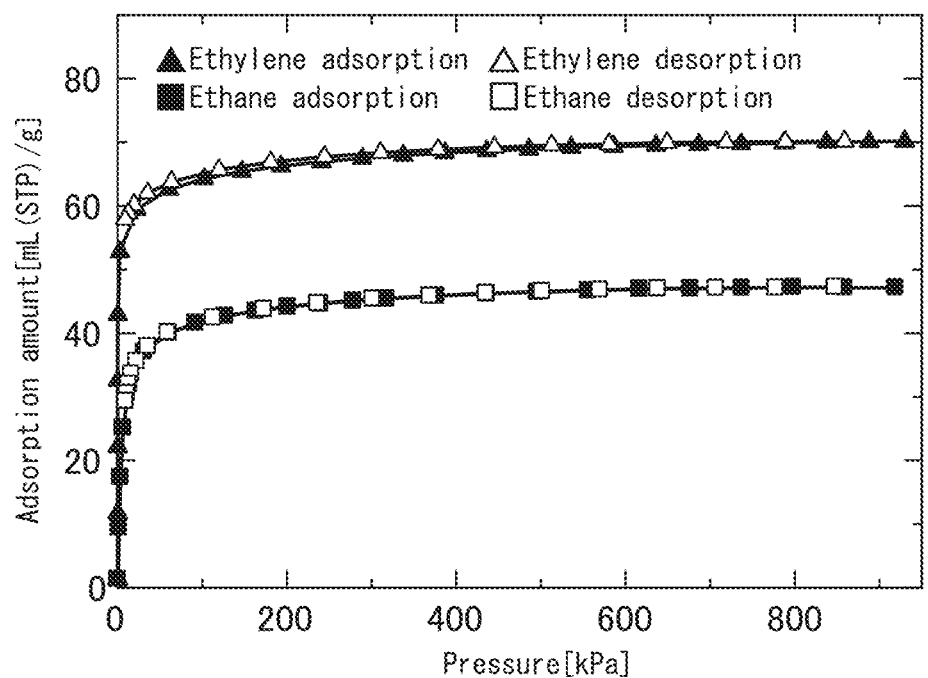
FIG. 6 illustrates an adsorption-desorption isotherm of ethylene and ethane at 0° C. for the adsorption material in Comparative Example 1.

For AgX zeolite (obtained from Sigma-Aldrich Japan LLC) as a typical adsorption material, an adsorption-desorption isotherm of ethylene and ethane at 0° C. was measured. The results are shown in FIG. 6.

Comparative Example 2

Figure 7:
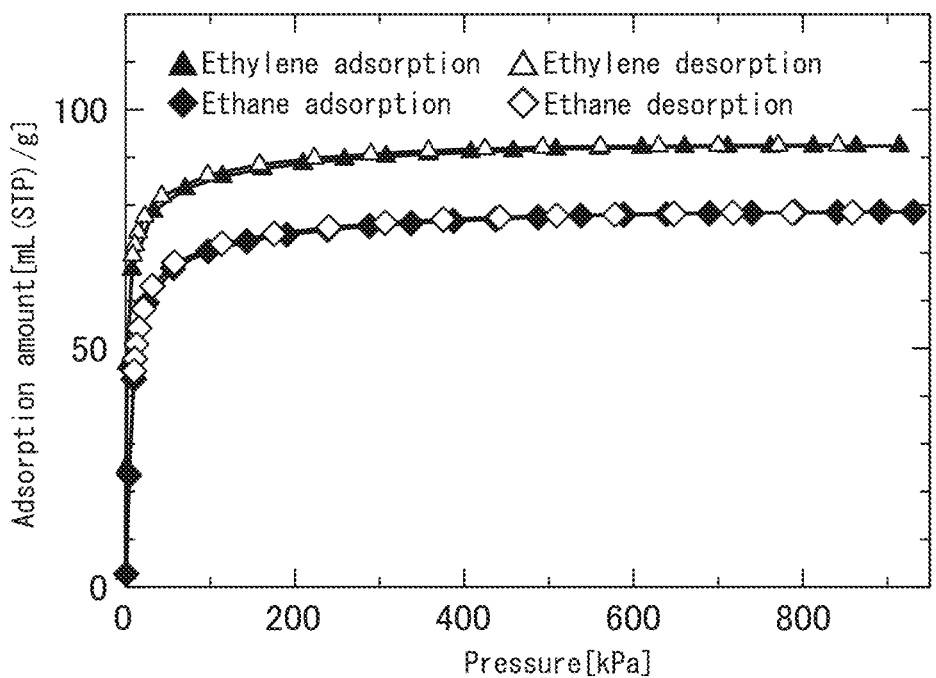
FIG. 7 illustrates an adsorption-desorption isotherm of ethylene and ethane at 0° C. for the adsorption material in Comparative Example 2.

For 13X zeolite (manufactured by Union Showa K.K.) as a typical adsorption material, an adsorption-desorption isotherm of ethylene and ethane at 0° C. was measured. The results are shown in FIG. 7.

Comparison among FIG. 3, FIG. 4, FIG. 5, FIG. 6, and FIG. 7 shows that a metal complex of the present invention selectively adsorbs ethylene within a pressure range of 0 to 1,000 kPa. Therefore, it is clear that a metal complex of the present invention is an excellent separating material of ethylene and ethane.

Example 5

Figure 8:
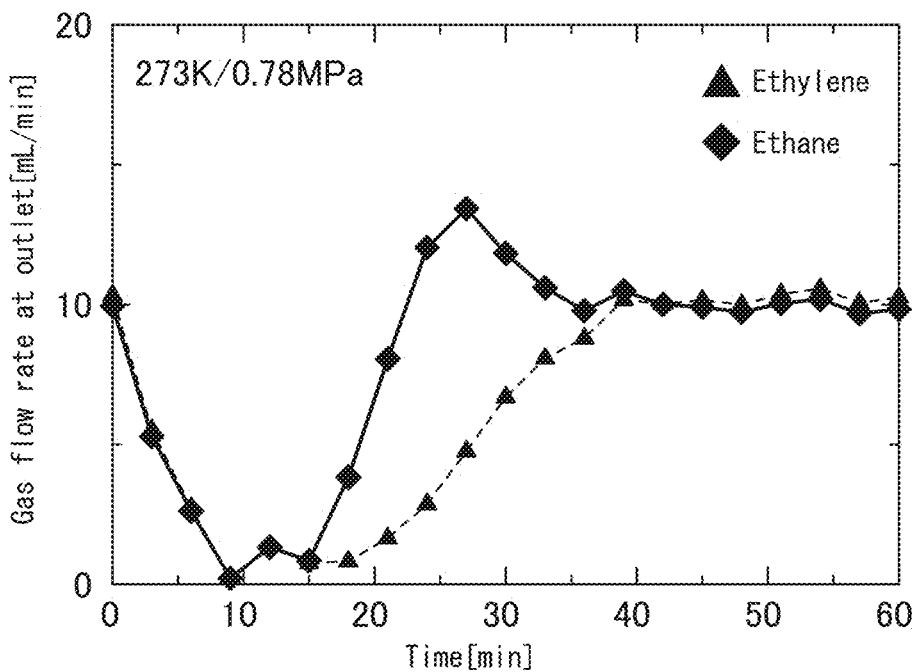
FIG. 8 shows a measurement result of a mixed gas separation experiment using a mixed gas of ethylene and ethane for the metal complex obtained in Example 1.

An adsorption tube (inner diameter 1.0 cm × length 20 cm) was packed with 5.4 g of the porous metal complex (1) obtained in Example 1. Subsequently, for activation of an adsorption material, heating and vacuum drawing were carried out at 150° C. for a packing prior to a study. After the temperature was cooled to room temperature, a pressure of 780 kPa was created using pure He gas, and under this condition, a mixture of ethylene 50% and ethane 50% was flowed into the adsorption tube at a flow rate of 20 mL/min to monitor the gas composition and the flow rate at the outlet of the adsorption tube with gas chromatography and a flowmeter. A function of the flow rate (mL/min) of each gas species and the time t (min) for the gas at the adsorption outlet is shown in FIG. 8. First, since two components are substituted for He gas in the dead volume, no components are detected with gas chromatography. After a certain period of time passed, the ethane component (black square) appears first, which is detected by an analysis with gas chromatography. On the other hand, ethylene (black triangle) is further adsorbed for a certain period of time, and finally reaches the breakthrough at a later time point. Therefore, ethylene can be selectively adsorbed by using an adsorption material constituted of a metal complex of the present invention.

<Adsorption Isotherm 4>

Figure 9:
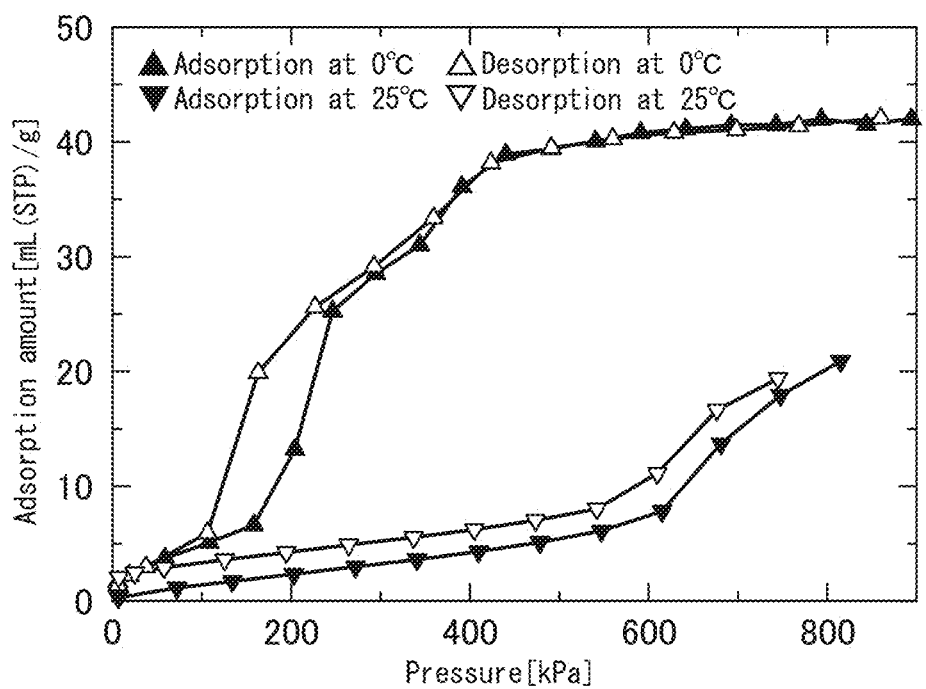
FIG. 9 illustrates an adsorption-desorption isotherm of ethylene at 0° C. and 25° C. for the metal complex obtained in Example 1.

For the porous metal complex (1) obtained in Example 1, an adsorption-desorption isotherm of ethylene at 0° C. and 25° C. was measured. The results are shown in FIG. 9. FIG. 9 reveals that the pressure at which adsorption begins of a metal complex of the present invention depends on temperature and can be controlled. By utilizing this characteristic, the degree of separation can be improved in temperature swing adsorption, compared with using the conventional separating materials.

<Adsorption Isotherm 5>

Figure 10:
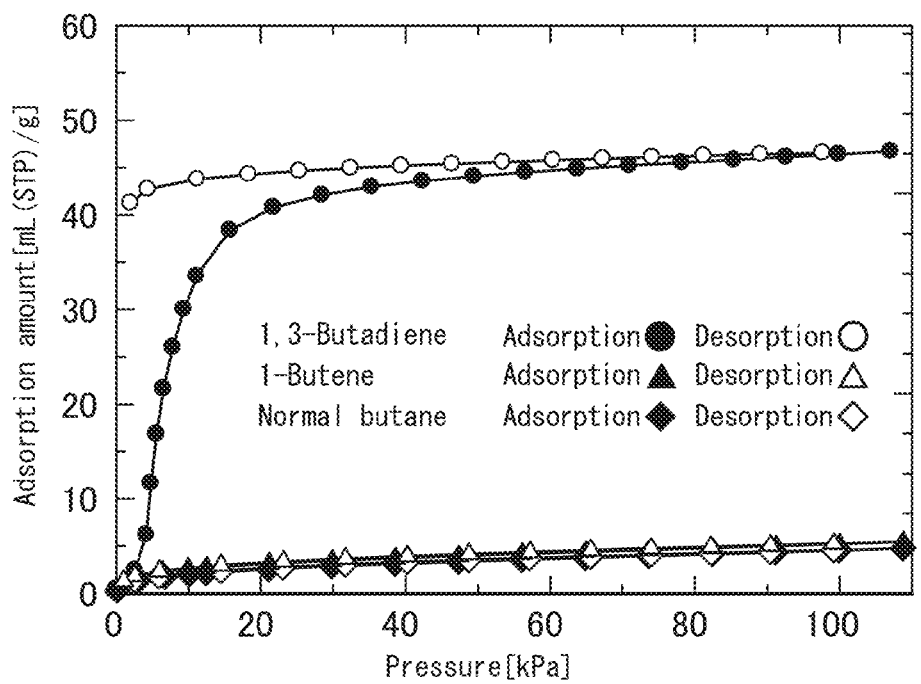
FIG. 10 illustrates an adsorption-desorption isotherm of 1,3-butadiene, 1-butene, and normal butane at 25° C. for the metal complex obtained in Example 1.

For the metal complex obtained in Example 1, an adsorption-desorption isotherm of 1,3-butadiene, 1-butene, and normal butane at 25° C. was measured. The results are shown in FIG. 10.

<Adsorption Isotherm 6>

Figure 11:
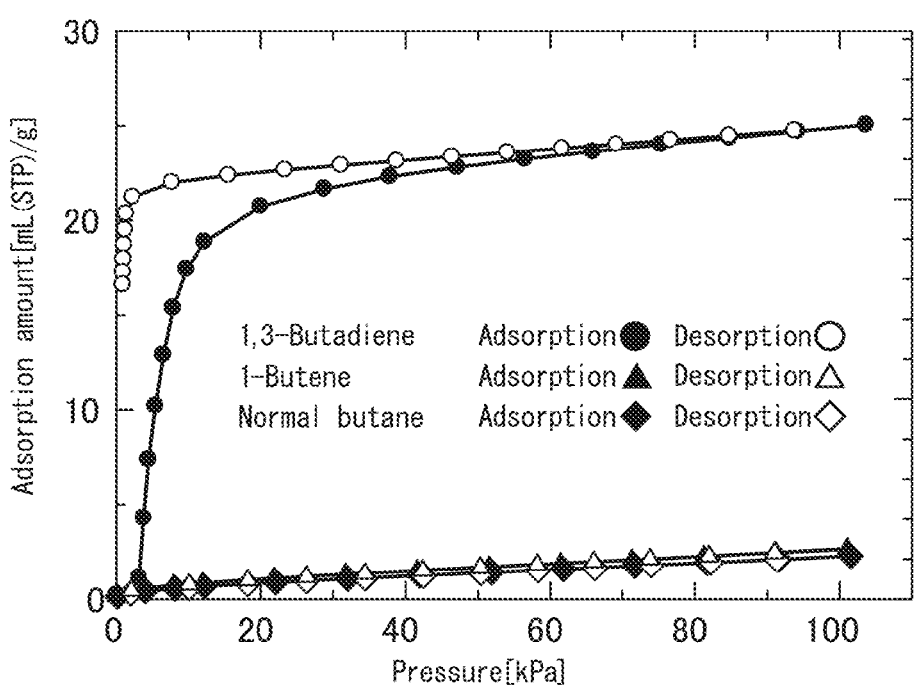
FIG. 11 illustrates an adsorption-desorption isotherm of 1,3-butadiene, 1-butene, and normal butane at 25° C. for the adsorption sheet in Example 4.

For the adsorption sheet (1) obtained in Example 4, an adsorption-desorption isotherm of each of 1,3-butadiene, 1-butene, and normal butane at 25° C. was measured. The results are shown in FIG. 11.

Comparative Example 3

Figure 12:
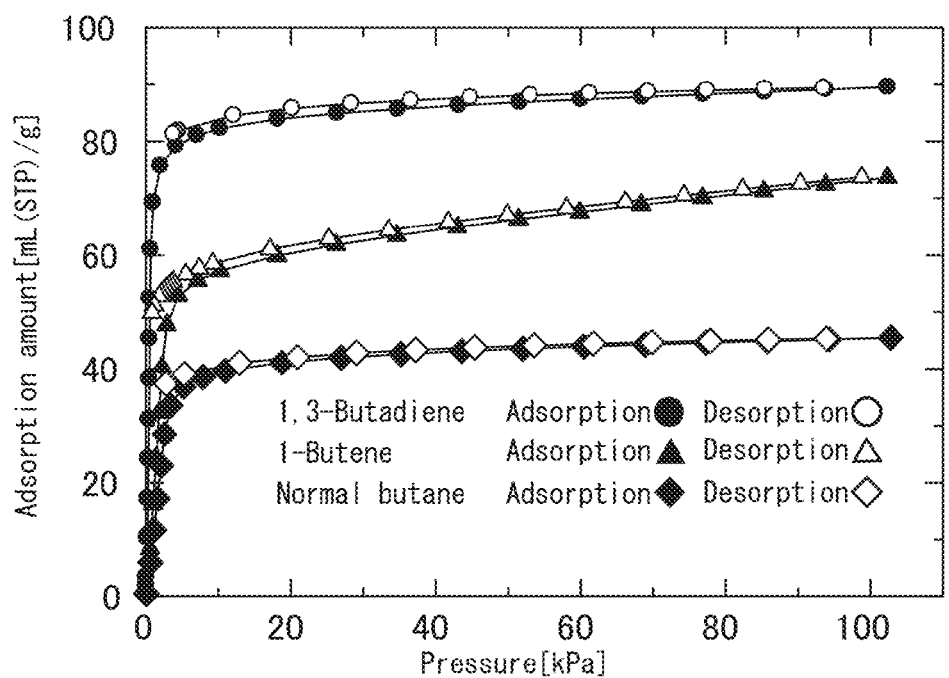
FIG. 12 illustrates an adsorption-desorption isotherm of 1,3-butadiene, 1-butene, and normal butane at 25° C. for the adsorption material in Comparative Example 3.

For NaY zeolite (HS-320, obtained from Wako Pure Chemical Industries, Ltd.) as a typical adsorption material, an adsorption-desorption isotherm of each of 1,3-butadiene, 1-butene, and normal butane at 25° C. was measured. The results are shown in FIG. 12.

Comparative Example 4

Figure 13:
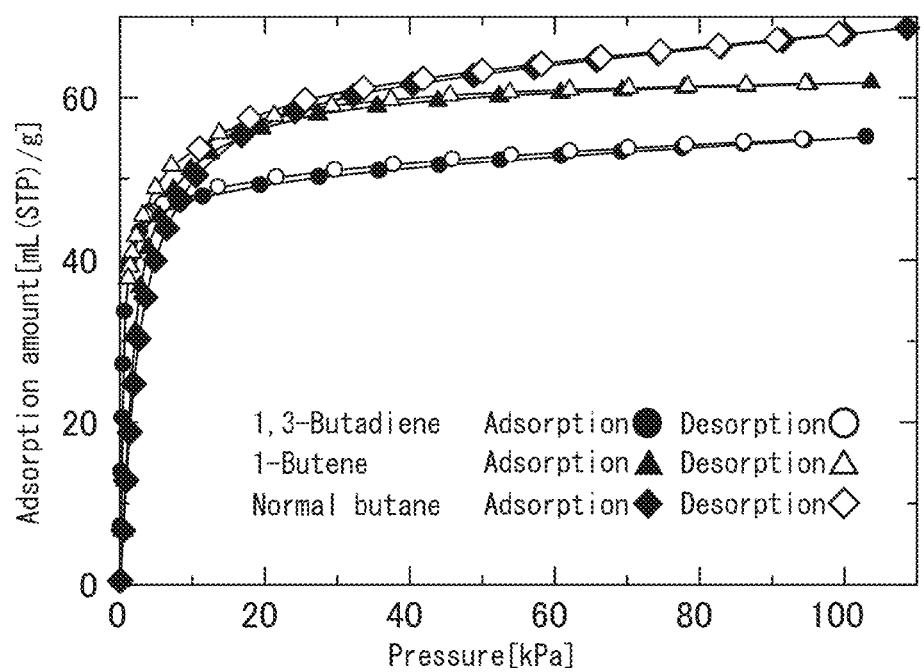
FIG. 13 illustrates an adsorption-desorption isotherm of 1,3-butadiene, 1-butene, and normal butane at 25° C. for the adsorption material in Comparative Example 4.

For Basosiv (registered trademark) M050 (obtained from Sigma-Aldrich Japan LLC) as a typical porous metal complex, an adsorption-desorption isotherm of each of 1,3-butadiene, 1-butene, and normal butane at 25° C. was measured. The results are shown in FIG. 13.

Example 6

Figure 14:
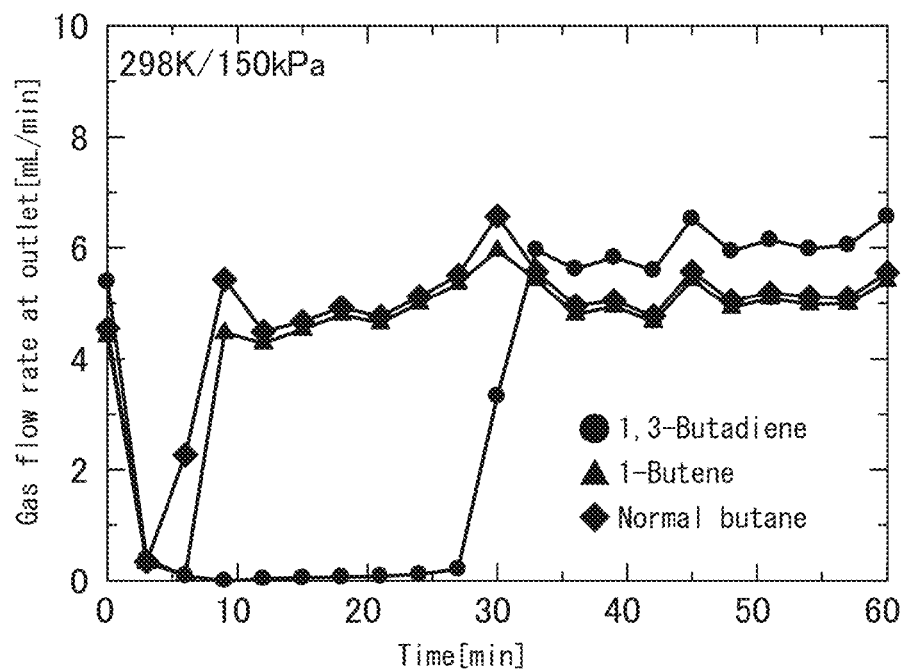
FIG. 14 shows a measurement result of a mixed gas separation experiment using a mixed gas of 1,3-butadiene with 1-butene and normal butane for the metal complex obtained in Example 1.

An adsorption tube (inner diameter 1.0 cm × length 20 cm) was packed with 4.8 g of the porous metal complex (1) obtained in Example 1. Subsequently, for activation of an adsorption material, heating and vacuum drawing were carried out at 150° C. for a packing prior to a study. After the temperature was cooled to room temperature, a pressure of 150 kPa was created using pure He gas, and under this condition, a mixture of 1,3-butadiene 38%, 1-butene 31%, and normal butane 31% was flowed into the adsorption tube at a flow rate of 15 mL/min to monitor the gas composition and the flow rate at the outlet of the adsorption tube with gas chromatography and a flowmeter. A function of the flow rate (mL/min) of each gas species and the time t (min) for the gas at the adsorption outlet is shown in FIG. 14. First, since three components are substituted for He gas in the dead volume, no components are detected with gas chromatography. Then, the normal butane component (black square) appears first and 1-butene (black triangle) appears next, which are detected by an analysis with gas chromatography. On the other hand, 1,3-butadiene (black circle) is further adsorbed for a certain period of time, and finally reaches the breakthrough at a later time point. Therefore, 1,3-butadiene can be selectively adsorbed by using an adsorption material constituted of a metal complex of the present invention.

<Adsorption Isotherm 7>

Figure 15:
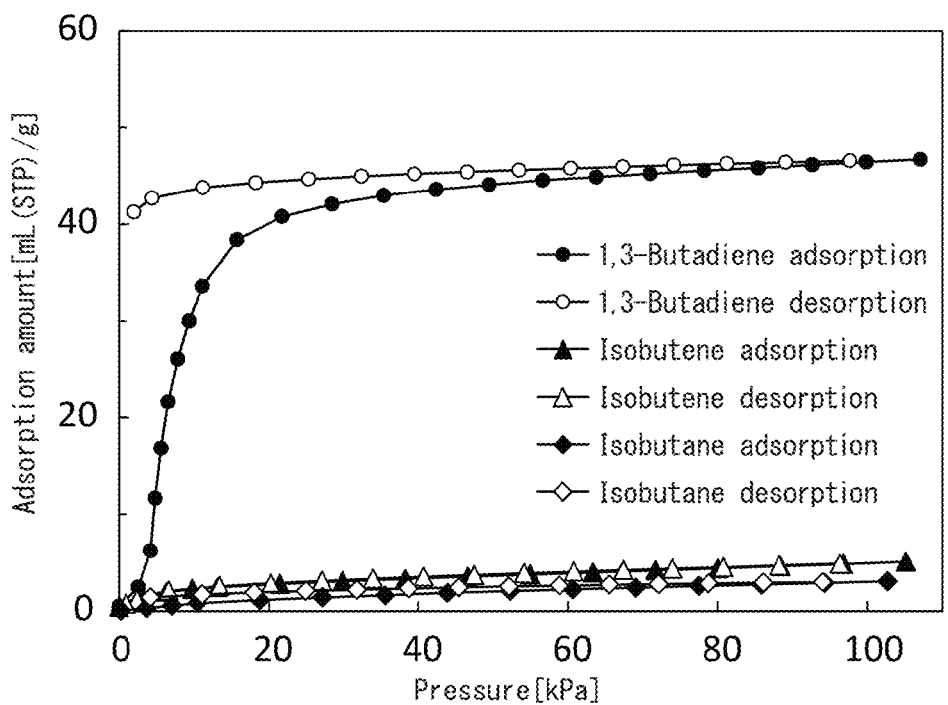
FIG. 15 illustrates an adsorption-desorption isotherm of 1,3-butadiene, isobutene, and isobutane at 25° C. for the metal complex obtained in Example 1.

For the metal complex obtained in Example 1, an adsorption-desorption isotherm of 1,3-butadiene, isobutene, and isobutane at 25° C. was measured. The results are shown in FIG. 15.

Comparative Example 5

Figure 16:
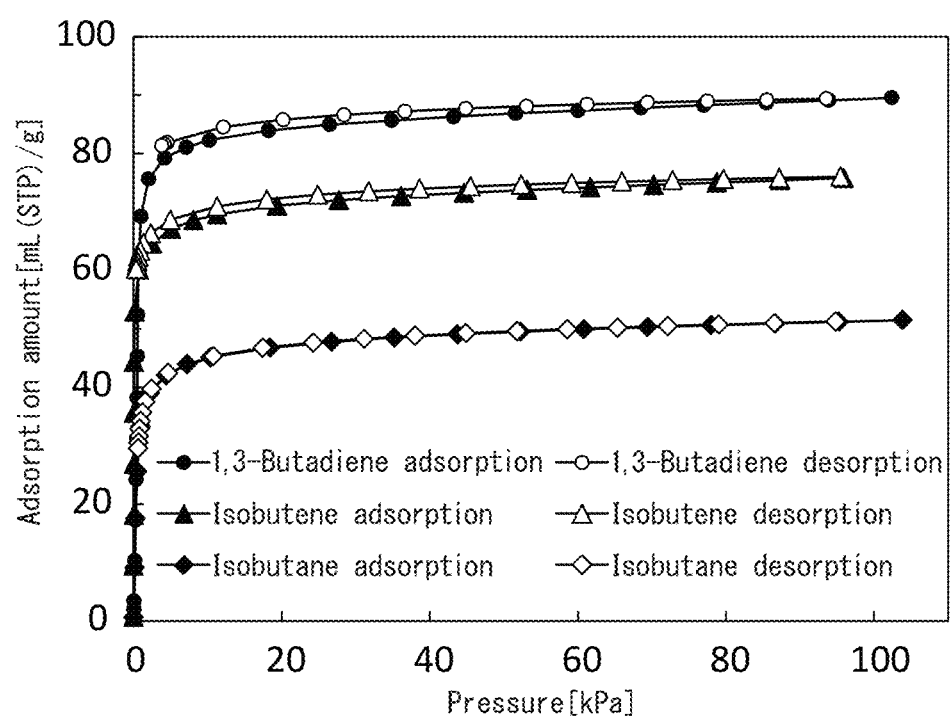
FIG. 16 illustrates an adsorption-desorption isotherm of 1,3-butadiene, isobutene, and isobutane at 25° C. for the adsorption material in Comparative Example 3.

For NaY zeolite as a typical adsorption material, an adsorption-desorption isotherm of each of 1,3-butadiene, isobutene, and isobutane at 25° C. was measured. The results are shown in FIG. 16.

Comparison among FIG. 10, FIG. 11, FIG. 12, FIG. 13, FIG. 14, FIG. 15, and FIG. 16 shows that a metal complex of the present invention selectively adsorbs 1,3-butadiene at room temperature. Therefore, it is clear that a metal complex of the present invention is an excellent separating material of 1,3-butadiene.

The invention claimed is:

1. A gas separating material that selectively separates a target gas defined as a hydrocarbon gas having a carbon-carbon double bond and having 2 or 4 carbon atoms from a mixed gas containing the target gas and a hydrocarbon gas having the same number of carbon atoms as the target gas, comprising a metal complex of:
2,3-pyrazinedicarboxylic acid;
at least one metal M ion selected from the group consisting of copper, zinc, and cadmium;
an organic ligand (B) capable of bidentate coordination to the metal ion, represented by the following general formula (2):

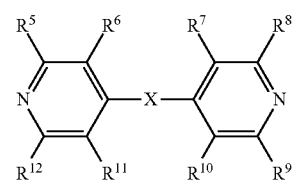

(2)

wherein the organic ligand (B) capable of bidentate coordination is 1,2-di(4-pyridyl)ethane represented by the general formula (2) wherein all of $R^5$, $R^6$, $R^7$, $R^8$, $R^9$, $R^{10}$, $R^{11}$, and $R^{12}$ are hydrogen atoms, and X is —$CH_2$—$CH_2$—, or 1,3-di(4-pyridyl)propane represented by the general formula (2) wherein all of $R^5$, $R^6$, $R^7$, $R^8$, $R^9$, $R^{10}$, $R^{11}$, and $R^{12}$ are hydrogen atoms, and X is —$CH_2$—$CH_2$—$CH_2$—; and the composition thereof is the following composition formula (I):

$$M^{2+}{}_2 A^{2-}{}_2 B \qquad (I)$$

wherein $M^{2+}$ is an ion of the metal M, $A^{2-}$ is 2,3-pyrazinedicarboxylate dianion, and B is an organic ligand (B) capable of bidentate coordination to the metal ion, and wherein the target gas is ethylene or 1,3-butadiene.

2. A method for separating a hydrocarbon gas having a carbon-carbon double bond and having 2 or 4 carbon atoms, the method comprising an adsorption step of bringing a mixed gas containing a target gas defined as a hydrocarbon gas having a carbon-carbon double bond and having 2 or 4 carbon atoms and a hydrocarbon gas having the same number of carbon atoms as the target gas into contact with a separating material to selectively adsorb the target gas on the separating material, and a subsequent regeneration step of desorbing the target gas adsorbed to the separating material from the separating material and collecting the target gas desorbed to separate the hydrocarbon gas having a carbon-carbon double bond and having 2 or 4 carbon atoms from the mixed gas, wherein the separating material comprises a metal complex of:

2,3-pyrazinedicarboxylic acid;

at least one metal M ion selected from the group consisting of beryllium, magnesium, calcium, strontium, barium, titanium, vanadium, chromium, manganese, iron, ruthenium, cobalt, rhodium, nickel, palladium, platinum, copper, zinc, and cadmium;

an organic ligand (B) capable of bidentate coordination to the metal ion, represented by the following general formula (1):

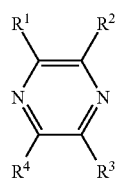
(1)

or the following general formula (2):

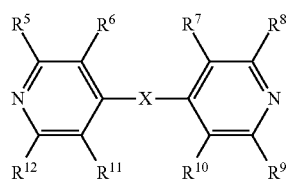
(2)

wherein X is any of —$CH_2$—, —$CH_2$—$CH_2$—, —$CH_2$—$CH_2$—$CH_2$—, —CH=CH—, —C≡C—, —O—, —S—, —S—S—, —N=N—, or —NHCO—, and $R^1$, $R^2$, $R^3$, $R^4$, $R^5$, $R^6$, $R^7$, $R^8$, $R^9$, $R^{10}$, $R^{11}$, and $R^{12}$ each of which may be the same or different, and are any of a hydrogen atom, an alkyl group having 1 to 4 carbon atoms that may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkyl amino group having 1 to 4 carbon atoms, a dialkyl amino group having 2 to 4 carbon atoms, an acylamino group having 2 to 4 carbon atoms, or a halogen atom; and the composition thereof is the following composition formula (I):

$$M^{2+}{}_2 A^{2-}{}_2 B \qquad (I)$$

wherein $M^{2+}$ is an ion of the metal M, $A^{2-}$ is 2,3-pyrazinedicarboxylate dianion, and B is an organic ligand (B) capable of bidentate coordination to the metal ion.

3. The separation method according to claim 2, wherein the target gas is ethylene, and the hydrocarbon gas having the same number of carbon atoms as the target gas is ethane.

4. The separation method according to claim 2, wherein the target gas is 1,3-butadiene, and the hydrocarbon gas having the same number of carbon atoms as the target gas is 1-butene, normal butane, or a mixture thereof.

5. The separation method according to claim 2, wherein the separation method is pressure swing adsorption.

6. The separation method according to claim 2, wherein the separation method is temperature swing adsorption.

7. A method for separating a hydrocarbon gas having a carbon-carbon double bond and having 2 or 4 carbon atoms, the method comprising a step of bringing a mixed gas containing a target gas defined as a hydrocarbon gas having a carbon-carbon double bond and having 2 or 4 carbon atoms and a hydrocarbon gas having the same number of carbon atoms as the target gas into contact a separation membrane to selectively permeate the target gas through the separation membrane, thereby obtaining a gas with a higher concentration of the target gas than the mixed gas, wherein the separation membrane comprises a porous support and a gas separating material deposited on a surface portion of the porous support, wherein the separating material comprises a metal complex of:

2,3-pyrazinedicarboxylic acid;

at least one metal M ion selected from the group consisting of beryllium, magnesium, calcium, strontium, barium, titanium, vanadium, chromium, manganese, iron, ruthenium, cobalt, rhodium, nickel, palladium, platinum, copper, zinc, and cadmium;

an organic ligand (B) capable of bidentate coordination to the metal ion, represented by the following general formula (1):

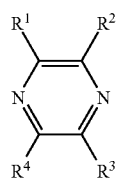
(1)

or the following general formula (2):

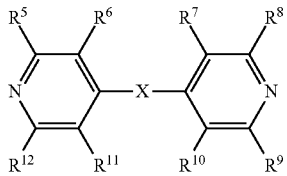
(2)

wherein X is any of —CH$_2$—, —CH$_2$—CH$_2$—, —CH$_2$—CH$_2$—CH$_2$—, —CH═CH—, —C≡C—, —O—, —S—, —S—S—, —N═N—, or —NHCO—, and R$^1$, R$^2$, R$^3$, R$^4$, R$^5$, R$^6$, R$^7$, R$^8$, R$^9$, R$^{10}$, R$^{11}$, and R$^{12}$ each of which may be the same or different, and are any of a hydrogen atom, an alkyl group having 1 to 4 carbon atoms that may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkyl amino group having 1 to 4 carbon atoms, a dialkyl amino group having 2 to 4 carbon atoms, an acylamino group having 2 to 4 carbon atoms, or a halogen atom; and the composition thereof is the following composition formula (I):

(I)

wherein M$^{2+}$ is an ion of the metal M, A$^{2-}$ is 2,3-pyrazinedicarboxylate dianion, and B is an organic ligand (B) capable of bidentate coordination to the metal ion.

8. A method for separating a hydrocarbon gas having a carbon-carbon double bond and having 2 or 4 carbon atoms, the method comprising a step of bringing a mixed gas containing a target gas defined as a hydrocarbon gas having a carbon-carbon double bond and having 2 or 4 carbon atoms and a hydrocarbon gas having the same number of carbon atoms as the target gas into contact a separation membrane to selectively permeate the target gas through the separation membrane, thereby obtaining a gas with a higher concentration of the target gas than the mixed gas, wherein the separation membrane comprises a polymer material and a gas separating material mixed and dispersed in the polymer material, wherein the separating material comprises a metal complex of:

2,3-pyrazinedicarboxylic acid;

at least one metal M ion selected from the group consisting of beryllium, magnesium, calcium, strontium, barium, titanium, vanadium, chromium, manganese, iron, ruthenium, cobalt, rhodium, nickel, palladium, platinum, copper, zinc, and cadmium;

an organic ligand (B) capable of bidentate coordination to the metal ion, represented by the following general formula (1):

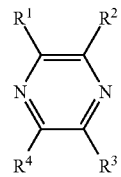
(1)

or the following general formula (2):

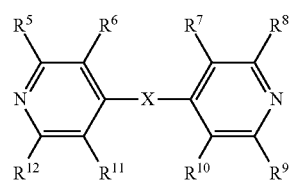
(2)

wherein X is any of —CH$_2$—, —CH$_2$—CH$_2$—, —CH$_2$—CH$_2$—CH$_2$—, —CH═CH—, —C≡C—, —O—, —S—, —S—S—, —N═N—, or —NHCO—, and R$^1$, R$^2$, R$^3$, R$^4$, R$^5$, R$^6$, R$^7$, R$^8$, R$^9$, R$^{10}$, R$^{11}$, and R$^{12}$ each of which may be the same or different, and are any of a hydrogen atom, an alkyl group having 1 to 4 carbon atoms that may have a substituent, an alkenyl group having 2 to 4 carbon atoms, an alkoxy group having 1 to 4 carbon atoms, a formyl group, an acyloxy group having 2 to 10 carbon atoms, an alkoxycarbonyl group having 2 to 4 carbon atoms, a nitro group, a cyano group, an amino group, a monoalkyl amino group having 1 to 4 carbon atoms, a dialkyl amino group having 2 to 4 carbon atoms, an acylamino group having 2 to 4 carbon atoms, or a halogen atom; and the composition thereof is the following composition formula (I):

(I)

wherein M$^{2+}$ is an ion of the metal M, A$^{2-}$ is 2,3-pyrazinedicarboxylate dianion, and B is an organic ligand (B) capable of bidentate coordination to the metal ion.

9. The separation method according to claim 2, wherein the target gas is ethylene or 1,3-butadiene.

10. The separation method according to claim 2, wherein the metal M is at least one selected from the group consisting of copper, zinc, and cadmium.

11. The separation method according to claim 2, wherein the metal M is copper.

12. The separation method according to claim 2, wherein the organic ligand (B) capable of bidentate coordination is pyrazine represented by the general formula (1) wherein all of R$^1$, R$^2$, R$^3$, and R$^4$ are hydrogen atoms.

13. The separation method according to claim 2, wherein the organic ligand (B) capable of bidentate coordination is 1,2-di(4-pyridyl)ethane represented by the general formula (2) wherein all of R$^5$, R$^6$, R$^7$, R$^8$, R$^9$, R$^{10}$, R$^{11}$, and R$^{12}$ are hydrogen atoms, and X is —CH$_2$—CH$_2$—, or 1,3-di(4-pyridyl)propane represented by the general formula (2) wherein all of R$^5$, R$^6$, R$^7$, R$^8$, R$^9$, R$^{10}$, R$^{11}$, and R$^{12}$ are hydrogen atoms, and X is —CH$_2$—CH$_2$—CH$_2$—.

* * * * *